(12) United States Patent
Hamon et al.

(10) Patent No.: US 8,697,604 B2
(45) Date of Patent: Apr. 15, 2014

(54) LABELING AGENTS FOR MASS SPECTROMETRY COMPRISING TERTIARY AMINES

(75) Inventors: Christian Hamon, Frankfurt am Main (DE); Karsten Kuhn, Dortmund (DE); Andrew Thompson, Cambridge (GB); Dieter Reuschling, Butzbach/Ostheim (DE); Juergen Schaefer, Lauterbach (DE)

(73) Assignee: Electrophoretics Limited, Cobham, Surrey (GB)

( * ) Notice: Subject to any disclaimer, the term of this patent is extended or adjusted under 35 U.S.C. 154(b) by 737 days.

(21) Appl. No.: 10/550,558

(22) PCT Filed: Mar. 18, 2004

(86) PCT No.: PCT/GB2004/001167
§ 371 (c)(1), (2), (4) Date: Aug. 21, 2006

(87) PCT Pub. No.: WO2004/086050
PCT Pub. Date: Oct. 7, 2004

(65) Prior Publication Data
US 2007/0023628 A1  Feb. 1, 2007

(30) Foreign Application Priority Data
Mar. 24, 2003 (GB) .................................. 0306756.8

(51) Int. Cl.
*C40B 40/00* (2006.01)
*G01N 33/68* (2006.01)

(52) U.S. Cl.
CPC ............ *G01N 33/68* (2013.01); *G01N 33/6848* (2013.01); *G01N 2458/15* (2013.01)
USPC ............... 506/13; 250/282; 436/173; 506/12; 506/41

(58) Field of Classification Search
CPC .............. G01N 2458/15; G01N 33/68; G01N 33/6848; G01N 33/6851; H01J 49/04
See application file for complete search history.

(56) References Cited

U.S. PATENT DOCUMENTS 3,890,357 A * 6/1975 Rubin et al. ................... 554/114
5,227,370 A * 7/1993 Kamachi et al. ................ 514/27
(Continued)

FOREIGN PATENT DOCUMENTS

JP       9-501830 A      2/1997
WO     WO 95/04160 A1  2/1995
(Continued)

OTHER PUBLICATIONS

Chemical Abstract No. 132:251034, V. Alezra et al., Tetrahedron Letters, 2000, 41(5), pp. 655-658.

(Continued)

*Primary Examiner* — Dirk Bass
(74) *Attorney, Agent, or Firm* — Arent Fox LLP

(57) ABSTRACT

Provided is a method for characterizing a molecule by mass spectrometry, which molecule comprises one or more free amino groups, which method comprises: (a) reacting one or more free amino groups in the molecule with a mass tag reagent comprising a reactive functionality capable of reacting with an amino group, and a tertiary amino group linked to the reactive functionality; and (b) characterizing the molecule by mass spectrometry.

8 Claims, 6 Drawing Sheets

Dimethylamino-acetic acid N-hydroxysuccinimide ester
Molecular Weight = 200.20

Toluene-4-sulfonate Dimethylamino-butyric acid N-hydroxysuccinimide ester
Molecular Weight = 229.26

Piperidin-1-yl-acetic acid N-hydroxysuccinimide ester
Molecular Weight = 240.26

2,6-Dimethyl-Piperidin-1-yl-acetic acid N-hydroxysuccinimide ester
Molecular Weight = 268.32

Morpholino-4-yl-acetic acid N-hydroxysuccinimide ester
Molecular Weight = 242.23

(56) References Cited

U.S. PATENT DOCUMENTS

| | | | |
|---|---|---|---|
| 5,260,475 | A | 11/1993 | Desmurs et al. |
| 5,281,698 | A | 1/1994 | Nitecki |
| 2003/0044864 | A1 | 3/2003 | Short et al. |
| 2003/0077616 | A1* | 4/2003 | Lomas .............................. 435/6 |
| 2004/0142378 | A1 | 7/2004 | Suzuki et al. |
| 2004/0219685 | A1 | 11/2004 | Pappin et al. |
| 2004/0220412 | A1* | 11/2004 | Pappin et al. ................ 548/542 |
| 2005/0048489 | A1* | 3/2005 | Thompson et al. .............. 435/6 |

FOREIGN PATENT DOCUMENTS

| | | | |
|---|---|---|---|
| WO | WO 00/20357 | A2 | 4/2000 |
| WO | 0168664 | A2 | 9/2001 |
| WO | WO 02/04936 | | 1/2002 |
| WO | WO 02/04936 | A1 | 1/2002 |
| WO | 02/29414 | A2 | 4/2002 |
| WO | 02/42427 | A2 | 5/2002 |
| WO | 02/066988 | A2 | 8/2002 |
| WO | 02/099435 | A1 | 12/2002 |
| WO | 03025576 | A2 | 3/2003 |

OTHER PUBLICATIONS

Chemical Abstract No. 115:255852, F. H. van der Steen et al., J. Org. Chem., 1991, 56(17) pp. 5147-5158.

Chemical Abstract No. 104:34269, S. Sakamoto et al., J. Antibiotics, 1985, 38(4), pp. 477-484.

Chemical Abstract No. 81:113568, K. Kimoto et al., Chemistry Letters, 1974, 8, pp. 859-860.

Chemical Abstract No. 74:52986, J. C. Micheau et al., Bulletin de la Societe Chimique de France, 1970, 11, pp. 4018-4023.

E. Haralambidou et al., "Effect of Distal Positional Isomerism on Peptide Fragmentation, A Comparison of Dimethylaminobenzylidene and Benzoyl Derivatives", *Organic Mass Spectrometry*, vol. 10, 1975, pp. 683-697.

R. A. Day et al., "N-Terminal Groups in Mass Spectrometry of Peptides, A Study Including Some New and Useful Derivatives, "*J. Org. Chem.*, vol. 38, No. 4, 1975, pp. 782-788.

M. R. Lewis et al., "A Facile, Water-Soluble Method for Modification of Proteins with DOTA. Use of Elevated Temperature and Optimized pH to Achieve High Specific Activity and High Chelate Stability in Radiolabeled Immunoconjugates", *Bioconjugate Chem.*, vol. 5, No. 6, 1994, pp. 565-576.

Corresponding Australian Office Action dated Nov. 11, 2010 (Three (3) pages).

Adamczyk, M., et al., "A Simple Method to Identify Cysteine Residues by Isotopic Labeling and Ion Trap Mass Spectrometry", John Wiley & Sons, Ltd., Rapid Communications in Mass Spectrometry, Jul. 21, 1999, vol. 13, pp. 1813-1817.

Bartlett-Jones, M., et al., "Peptide Ladder Sequencing by Mass Spectrometry Using a Novel, Volatile Degradation Reagent", John Wiley & Sons, Ltd., Rapid Communications in Mass Spectrometry, vol. 8, Jul. 22, 1994, pp. 737-742.

Bonetto, V., et al., "C-Terminal Sequence Determination of Modified Peptides by MALDI MS", Plenum Publishing Corporation, Journal of Protein Chemistry, vol. 16, No. 5, Jul. 1997, pp. 371-374.

Brancia, F. L., et al., "Improved matrix-assisted laser desorption/ionization mass spectrometric analysis of tryptic hydrolysates of proteins following guanidination of lysine-containing peptides", John Wiley & Sons, Ltd., Rapid Communications in Mass Spectrometry, vol. 14, Sep. 10, 2000, pp. 2070-2073.

Cardenas, M.S., et al., "On-line Derivatization of Peptides for Improved Sequence Analysis by Micro-column Liquid Chromatography Coupled with Electrospray Ionization-Tandem Mass Spectrometry", John Wiley & Sons, Ltd., Rapid Communications in Mass Spectrometry, vol. 11, Jun. 29, 1997, pp. 1271-1278.

Gaskell, S., "Electrospray: Principles and Practice", John Wiley & Sons, Ltd., Journal of Mass Spectrometry, vol. 32, May 1, 1997, pp. 677-688.

Goodlett, D.R., et al., "Protein Identification with a Single Accurate Mass of a Cysteine-Containing Peptide and Constrained Database Searching", American Chemical Society, Analytical Chemistry, vol. 72, No. 6, Mar. 15, 2000, pp. 1112-1118.

Griffiths, W.J., et al., "Negative-ion Electrospray Mass Spectra of Peptides Derivatized with 4-Aminonaphthalenesulphonic Acid", John Wiley & Sons, Ltd., Rapid Communications in Mass Spectrometry, vol. 9, May 19, 1995, pp. 667-676.

Gygi, S.P., et al., "Quantitative analysis of complex protein mixtures using isotope-coded affinity tags", Nature America Inc., Nature Biotechnology, vol. 17, Oct. 1999, pp. 994-999.

Han, D.K., et al., "Quantitative profiling of differentiation-induced microsomal proteins using isotope-coded affinity tags and mass spectrometry", National Biotechnology, vol. 19, No. 10, Oct. 2001, pp. 946-951.

Karas, M., et al., "Ionization in matrix-assisted laser desorption/ionization: singly charged molecular ions are the lucky survivors", John Wiley & Sons, Ltd., Journal of Mass Spectrometry, vol. 25, Oct. 3, 1999, pp. 1-12.

Kaufmann, R., et al., "Post-source Decay and Delayed Extraction in Matrix-assisted Laser Desorption/Ionization-Reflection Time-of-Flight Mass Spectrometry. Are Three Trade-offs?", John Wiley & Sons, Ltd., Rapid Communications in Mass Spectrometry, vol. 10, No. 10, Jun. 26, 1996, pp. 1199-1208.

Keough, T., et al., "Atmospheric pressure matrix-assisted laser desorption/ionization ion trap mass spectrometry of sulfonic acid derivatized tryptic peptides", John Wiley & Sons, Ltd., Rapid Communications in Mass Spectrometry, vol. 15, Issue 23, Dec. 15, 2001, pp. 2227-2239.

Liu, H. et al., "Multidimensional Separations for Protein/Peptide Analysis in the Post-Genomic Era", BioTechniques vol. 32, No. 4, Apr. 2002, pp. 898-911.

Mann, M., et al., "Use of Mass Spectrometric Molecular Weight Information to Identify Proteins in Sequence Databases", John Wiley & Sons, Ltd., Biological Mass Spectrometry, vol. 22, Feb. 26, 1993, pp. 338-345.

Mizhiritskii, M., et al., "Trends in peptide chemistry. 1. New life of "old" coupling reagent", Chimica Oggi Chemistry Today, vol. 20, May 2002, pp. 41-44.

Mizhiritskii, M., et al., Trends in peptide chemistry. 2. Protected unprotected amino acids, Chimica Oggi Chemistry Today, vol. 20, May 2002, pp. 10-12.

Moini, M., "Capillary electrophoresis mass spectrometry and its application to the analysis of biological mixtures", Springer-Verlag, Analytical Bioanalytical Chemistry, vol. 373, Apr. 30, 2002, pp. 466-480.

Morand, K.L., et al., "Advances in high-throughput mass spectrometry", PhamaPress Ltd, Current Opinion in Drug Discovery & Development, vol. 4, No. 6, Nov. 2001, pp. 729-735.

Pappin, D.J.C., et al., "Rapid identification of proteins by peptide-mass fingerprinting", Current Biology, vol. 3, No. 6, Jun. 1993, pp. 327-332.

Polce, M.J., et al., "Dissociation of the peptide bond in protonated peptides", John Wiley & Sons, Ltd., Journal of Mass Spectrometry, vol. 35, Oct. 7, 2000, pp. 1391-1398.

Roth, K.D.W., et al., "Charge Derivatization of Peptides for Analysis by Mass Spectrometry", John Wiley & Sons, Ltd., Mass Spectrometry Reviews, vol. 17, Sep. 29, 1998, pp. 255-274.

Schlosser, A., et al., "Five-membered ring formation in unimolecular reactions of peptides: a key structural element controlling low-energy collision-induced dissociation of peptides", John Wiley & Sons, Ltd., Journal of Mass Spectrometry, vol. 35, Oct. 6, 2000, pp. 1382-1390.

Sechi, S., "A method to identify and simultaneously determine the relative quantities of proteins isolated by gel electrophoresis", John Wiley & Sons, Ltd., Rapid Communications in Mass Spectrometry, vol. 16, Issue 15, Aug. 15, 2002, pp. 1416-1424.

Sechi, S., et al., "Modification of Cysteine Residues by Alkylation. A Tool in Peptide Mapping and Protein Identification", American Chemical Society, Analytical Chemistry, vol. 70, No. 24, Dec. 15, 1998, pp. 5150-5158.

Shen, Y., et al., "High-Efficiency Capillary Isoelectric Focusing of Peptides", American Chemical Society, Analytical Chemistry, vol. 72, No. 9, May 1, 2000, pp. 2154-2159.

(56) References Cited

OTHER PUBLICATIONS

Sherman, N.E., et al., "A Novel N-Terminal Derivative Designed to Simplify Peptide Fragmentation", Proceedings of the 43rd ASMS Conference on Mass Spectrometry and Allied Topics, Atlanta, GA, May 21-26, 1995, pp. 626-627.

Smolka, M.B., et al., "Optimization of the Isotope-Coded Affinity Tag-Labeling Procedure for Quantitative Proteome Analysis", Academic Press, Analytical Biochemistry, vol. 297, Sep. 12, 2001, pp. 25-31.

Steen, H. et al., "Analysis of Bromotryptophan and Hydroxyproline Modifications by High-Resolution, High-Accuracy Precursor Ion Scanning Utilizing Fragment Ions with Mass-Deficient Mass Tags", American Chemical Society, Analytical Chemistry, vol. 74, No. 24, Dec. 15, 2002, pp. 6230-6236.

Stults, J.T., et al., "Amino-Terminal Derivatization of Peptides Yields Improved CAD Spectra", Proceedings of the 37th ASMS Conference on Mass Spectrometry and Allied Topics, May 21-26, 1989, Miami Beach, FL, p. 856-857.

Stults, J.T., "Amino-Terminal Quaternary Ammonium Derivatives of Peptides Alter Fragmentation by Electrospray Ionization/Low-Energy Collisionally Activated Dissociation", Proceedings of the 40th ASMS Conference on Mass Spectrometry and Allied Topics, Washington DC, May 31-Jun. 5 1992, p. 1815-1816.

Tang, X.J., et al., "Fragmentation Reactions of Multiply-Protonated Peptides and Implications for Sequencing by Tandem Mass Spectrometry with Low-Energy Collision-Induced Dissociation", American Chemical Society, Analytical Chemistry, vol. 65, Oct. 1993, pp. 2824-2834.

Tang, Q., et al., "Two-Dimensional Analysis of Recombinant *E. coli* Proteins Using Capillary Isoelectric Focusing Electrospray Ionization Mass Spectrometry", American Chemical Society, Analytical Chemistry, vol. 69, No. 16, Aug. 15, 1997, pp. 3177-3182.

Washburn, M.P., et al., "Analysis of Quantitative Proteomic Data Generated via Multidimensional Protein Identification Technology", American Chemical Society, Analytical Chemistry, vol. 74, No. 7, Apr. 1, 2002, pp. 1650-1657.

Washburn, M.P., et al., "Analysis of the microbial proteome", Elsevier Science Ltd., Current Opinion in Microbiology, vol. 3, 2000, pp. 292-297.

Washburn, M.P., et al., "Large-scale analysis of the yeast proteome by multidimensional protein identification technology", Nature Publishing Group, Nature Biotechnology, vol. 19, Mar. 2001, pp. 242-247.

Wolters, D.A., et al., "An Automated Multidimensional Protein Identification Technology for Shotgun Proteomics", American Chemical Society, Analytical Chemistry, vol. 73, No. 23, Dec. 1, 2001, pp. 5683-5690.

Wysocki, V.H., et al., "Mobile and localized protons: a framework for understanding peptide dissociation", John Wiley & Sons, Ltd., Journal of Mass Spectrometry, vol. 35, Oct. 9, 2000, pp. 1399-1406.

Yates III, J.R., et al., "Peptide Mass Maps: A Highly Informative Approach to Protein Identification", Academic Press, Inc., Analytical Biochemistry, vol. 214, Mar. 26, 1993, pp. 397-408.

Brancia, F.L., et al., "A combination of chemical derivatisation and improved bioinformatic tools optimises protein identification for proteomics", WILEY-VCH Verlag GmbH, Electrophoresis 2001, vol. 22, pp. 552-559.

Abdel-Baky, S., et al., Gas Chromatography/Electron Capture Negative-Ion Mass Spectrometry at the Zeptomole Level, American Chemical Society, Analytical Chemistry, vol. 63, 1991, pp. 2986-2989.

Bian, N., et al., "Detection Via Laser Desorption and Mass Spectrometry of Multiplex Electrophore-labeled Albumin", Rapid Communications in Mass Spectrometry, vol. 11, Sep, 8, 1997, pp. 1781-1784.

MacCoss, M.J., et al., "Probability-Based Validation of Protein Identifications Using a Modified SEQUEST Algorithm", American Chemical Society, Analytical Chemistry, vol. 74, No. 1, 2002, pp. 5593-5599.

Yates III, J.R., et al., "Mining Genomes: Correlating Tandem Mass Spectra of Modified and Unmodified Peptides to Sequences in Nucleotide Databases", American Chemical Society, Analytical Chemistry, vol. 67, No. 18, Sep. 15, 1995, pp. 3202-3210.

Solomons, T.W.Graham, "Fundamentals of Organic Chemistry", John Wiley & Sons, Inc., 5th Edition, pp. 743-744, 760-763, 789-794, and 987.

J.W. Back, et al., "A New Crosslinker for Mass Spectrometric Analysis of the Quaternary Structure of Protein Complexes", 2001, pp. 222-227, vol. 12 (Six (6) pages), American Society for Mass Spectrometry.

David J. Harvey, "N-2(2-Diethylamino)ethyl-4-aminobenzamide derivative for high sensitivity detection and structure determination of N-linked carbohydrates", Rapid Communications in Mass Spectrometry, 2000, pp. 862-871, vol. 14, Issue 10 (Eleven (11) pages).

Japanese Office Action dated Feb. 9, 2010 (Three (3) pages).

* cited by examiner

LABELING AGENTS FOR MASS SPECTROMETRY COMPRISING TERTIARY AMINES

This invention relates to methods of labelling non-volatile analyte molecules particularly biomolecules with markers that assist in the purification, detection and analysis (including quantitative analysis) of the labelled biomolecule particularly with analysis by Electrospray Ionisation (ESI) and Matrix Assisted Laser Desorption Ionisation (MALDI) Mass Spectrometry. Specifically this invention relates to tertiary amino compounds linked to reactive functionalities that enable the labelling of amino groups in natural or synthetic biomolecules.

Mass spectrometry is a powerful tool in protein and peptide identification and structure analysis. Matrix-assisted laser desorption ionisation time of flight mass spectrometry (MALDI TOF MS) has become a robust tool for the identification of 2-D gel separated proteins by Peptide Mass Fingerprinting (Mann, Hojrup et al. 1993; Pappin, Höjrup et al. 1993; Yates, Speicher et al. 1993) while Electrospray Ionisation (ESI)-tandem mass spectrometry (MS/MS) coupled to high-performance liquid chromatography (HPLC) is emerging as the preferred technique for the analysis of digests of complex protein mixtures particularly in combination with novel peptide separation and isolation techniques, such as ICAT(Gygi, Rist et al. 1999; Han, Eng et al. 2001; Smolka, Zhou et al. 2001) and MudPIT(Washburn and Yates 2000; Washburn, Wolters et al. 2001; Wolters, Washburn et al. 2001; Washburn, Ulaszek et al. 2002).

Sequence information for peptides analysed by both ESI and MALDI can be obtained from their product-ion spectra after collision-induced dissociation (CID) of the protonated molecule with tandem mass spectrometric analysis. ESI-MS is however, particularly useful for peptide identification as it tends to produce better MS/MS spectra. This is due to a number of features of the ESI process. Ionisation by ESI imparts a very small amount of kinetic energy to the ions formed. In addition, atmospheric pressure ion sources rapidly equilibrate ion temperature through collisions. This allows, controlled acceleration of ions to impart precise amounts of kinetic energy. In addition, it is usual to couple ESI to tandem mass anlysers with a dedicated collision cell which provides a controlled environment for low energy CID. Similarly, ion traps with their high operating pressure and selective activation of ions also provide controlled CID conditions. In contrast, MALDI generates energetic ions in a near-vacuum, that typically fragment with a different mechanism to ESI. It is also unusual to have a collision cell in a MALDI instrument and the few instruments that do have a collision cell, typically operate at higher collision energies than the corresponding ESI instrumentation. Furthermore, ESI generates ions with higher charge states (Gaskell 1997) than MALDI, which typically produces singly charged ions (Karas, Gluckmann et al. 2000). This means that larger ions can be analysed in the functional range of the instrument and peptides with higher charge states generally give better CID spectra (Tang, Thibault et al. 1993) as more highly charged species give rise to multiple ion series providing redundant sequence information and sequence information from both termini of the peptide: the currently accepted model of peptide scission during CID requires protonation of the peptide backbone followed by nucleophilic attack of the carbonyl moiety of the protonated amide by the next N-terminal carbonyl residue in the peptide chain to form a relatively stable oxazolone leading to scission of the amide bond (Polce, Ren et al. 2000; Schlosser and Lehmann 2000) yielding two main fragment ion series of type b (containing N-terminal residues) and y (C-terminal residues), respectively. Higher charge states promote the formation of both ion classes ensuring a better chance of complete elucidation of peptide sequences. However, there are many pitfalls in the determination of peptide sequences by MS/MS. The b-series ions, for example, can lose the carbonyl moiety producing a further ion series, dubbed a type ions. A further problem, for CID of peptides is distinguishing isomeric (leucine and isoleucine) or isobaric (lysine and glutamine) amino acids.

It has been shown, however, that chemical modification of peptides can improve the results of MS/MS analyses. For instance, derivatisation of lysine allows glutamine to be distinguished (Bonetto, Bergman et al. 1997; Cardenas, van der Heeft et al. 1997). Sulphonic acid derivatives of the alpha-amino functionality of peptides have been shown to enhance fragmentation efficiency in MALDI-Ion Trap analysis of peptides with improved spectra for certain classes of peptides that typically give poor MS/MS spectra in the ion trap, such as peptides containing aspartic and glutamic acid (Keough, Lacey et al. 2001). The strongly acidic functionality facilitates protonation of the amide backbone of singly charged peptides in MALDI leading to increased fragmentation. Sulphonic acid derivatives of peptides have also been shown to improve sensitivity of negative ion mode ESI-MS (Griffiths, Lindh et al. 1995). Aminonaphthalenesulphonic acid derivatives of peptides produce [M−H−] ions with good efficiency, which makes it possible to take advantage of the lower noise levels of the negative ion mode giving very high sensitivity.

Quaternary ammonium derivatisation reagents have been tested for a number of mass spectrometry techniques, including Fast Atom Bombardment (FAB) (Stults, Halualani et al. 1989), MALDI TOF (Bartlet-Jones, Jeffery et al. 1994) and ESI (Stults 1992) for the analysis of peptides. Typically sensitivity is not significantly enhanced by quaternary ammonium derivatisation in FAB, MALDI or ESI, with reduction in sensitivity reported in ESI applications (Stults 1992). However, fragmentation behaviour is modified by these sorts of tags: quaternary ammonium ion derivatised peptides show greater predominance of a- and d-series ions from peptides derivatised at the N-terminus and more abundant y-, v- and w-series for peptides derivatised on Lysine at the C-terminus (Roth, Huang et al. 1998).

As a further example, guanidination of lysine has been shown to enhance the sensitivity of the detection of lysine containing peptides in MALDI analyses (Bonetto, Bergman et al. 1997; Brancia, Oliver et al. 2000; Brancia, Butt et al. 2001). Similarly, N-succinimidyl-2-(3-pyridylacetate) (SPA) has been used for the derivatisation of peptides for ESI-MS/MS analysis (Sherman, Yates et al. 1995; Cardenas, van der Heeft et al. 1997). The SPA reagent has been shown to alter the CID fragmentation pathway, resulting in less complex product-ion spectra and the promotion of the formation of b-type ions. The reaction of SPA with peptides occurs selectively at the alpha and epsilon amino functions but not with the guanidino function of arginine.

Various other reagents for derivatising peptides have been also been developed. Halogenated compounds, particularly halogenated aromatic compounds are well known electrophores, i.e. they pick up thermal electrons very easily. A variety of derivatisation reagents based on fluorinated aromatic compounds (Bian N. et al., Rapid Commun Mass Spectrom 11(16): 1781-1784, "Detection via laser desorption and mass spectrometry of multiplex electrophore-labelled albumin." 1997) have been developed for electron capture detection, which is a highly sensitive ionisation and detection process that can be used with negative ion mass spectrometry (Abdel-Baky S. & Giese R. W., Anal. Chem. 63(24):2986-2989, "Gas chromatography/electron capture negative-ion mass spectrometry at the zeptomole level." 1991).

Each type of derivitisation reagent that has been disclosed in the prior art has different benefits and limitations, which depend on the method of ionisation used and on the methods of mass analysis used (for a review see Roth et al., Mass Spectrometry Reviews 17:255-274, "Charge derivatisation of peptides for analysis by mass spectrometry", 1998). The mechanism by which sensitivity is enhanced may also be different for each type of group. Some derivitisation methods increase basicity and thus promote protonation and charge localisation, while other methods increase surface activity of the tagged peptides, which improves sensitivity in surface desorption techniques like Matrix Assisted Laser Desorption Ionisation (MALDI) and Fast Atom Bombardment (FAB). Negative ion mass spectrometry is often more sensitive because there is less background noise.

Most of the reactions discussed above have been performed on peptides rather than on whole proteins. In general, the kinetics of peptide derivatisation reactions are more favourable than the corresponding reactions of whole proteins, probably due to the reduced steric accessibility of reactive groups in large, folded polypeptides. Very little work has been reported on labelling of large polypeptides with any of the reagents above, which is an object of this invention.

It is an object of this invention to provide methods and labels that can be used to produce protect amino groups in biomolecules, particularly proteins while retaining a functionality that can still protonate, which is advantageous for purification of labelled biomolecules and is also advantageous for analysis of the labelled biomolecules by mass spectrometry.

It is an object of this invention to provide compounds which have desirable features as mass labels and methods for the use of those compounds to provide improved mass spectra of associated analytes.

In a first aspect of this invention there is provided a Basic Mass Tag reagent with the following general structure:

Tertiary amino group—Linker-Reactive Functionality where the Basic Mass Tag reagent is preferably selected from the group comprising:

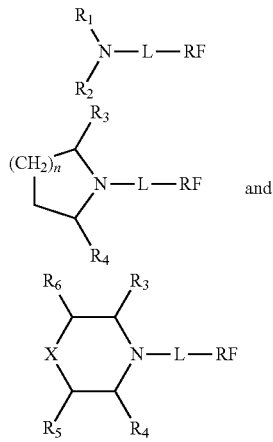

where $R_1$, $R_2$, can be alkyl or aralkyl such as independently methyl, ethyl, propyl, iso-propyl, cyclohexyl, benzyl or substituted benzyl and preferably methyl, ethyl or iso-propyl;

$R_3$, $R_4$, $R_5$ and $R_6$ can be alkyl, such as independently, methyl, ethyl, propyl, iso-propyl or hydrogen and preferably methyl or hydrogen;

n can be comprised between 0 and 2 and preferably 2;

X can be independently an N-alkyl (where alkyl is referred as a methyl, ethyl, propyl, iso-propyl or cyclohexyl), S or O and preferably X is O;

and where RF, the reactive functionality, is preferably selected from the group comprising active esters of carbonic acids, alkenyl sulphones, haloalkanes, maleimides, isocyanates, isothiocyanates, ketones, aldehydes, sulphonyl-halides, carboxylic-halides, anhydride esters and alkenes and preferably active esters of carbonic acid such as independently N-hydroxysuccinimide esters, nitrophenyl esters, trichlorophenyl esters, pentafluorophenyl esters, hydroxybenzotriazole esters and hydroxyazabenzotriazole esters, (see Mizhiritskii and Shpernat 2002);

and where L, the linker, can be an alkylene linker such as independently —$(CH_2)n$— and substituted —$(CH_2)n$— (where n is comprised between 1 to 5), and phenylene such as —$(C_6H_4)$— and preferably —$CH_2$— and —$(CH_2)_3$—.

The substituents mentioned above are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or 1). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination, of two or more of the substituents and/or functional groups defined above.

In a preferred embodiment of the first aspect of this invention the Basic Mass Tag (BMT) reagent has a characteristic isotope abundance distribution. In one such embodiment, the BMT is substituted with one or more halogen atoms or with atoms of stable isotopes such as deuterium, $^{13}C$ and/or $^{15}N$. In a second embodiment, the BMT reagent comprises a mixture of two or more isotopes of the same compound, such that the reagent imparts are a characteristic distribution of isotopes to a population of labelled ions.

The invention also provides an array of mass tags for labelling one or more molecules to be characterised by mass spectrometry, which array comprises two or more mass tags as defined above. In one embodiment, every mass tag in the array has the same chemical structure, and each mass tag in the array is an isotopomer of the other mass tags in the array such that each mass tag in the array has a different mass. These arrays of tags are useful for investigating a plurality of analytes simultaneously.

In a second typical aspect of this invention there is provided a method of analysing a polypeptide comprising the steps of:
1. labelling free amino functionalities in the polypeptide with a reactive, tertiary-amino group containing reagent;
2. cleaving the polypeptide with a sequence specific cleavage reagent;
3. labelling the free amino groups generated in the peptides by the cleavage reagent with a second amino-reactive reagent; and
4. analysing the cleavage peptides by mass spectrometry.

In preferred embodiments of this aspect of the invention, the labelled peptides are separated by application of one or more analytical separation techniques prior to analysis by mass spectrometry. In more preferred, embodiments the labelled peptides generated by the cleavage reagent are purified by analytical separation of the peptides using strong cation exchange (SCX) chromatography. In still more preferred embodiments, the labelled peptides are purified by analytical separation of the peptides using SCX as part of a multi-dimensional analytical separation in which a number of different separation techniques are applied in sequence to the labelled peptides.

The invention also provides a kit comprising the Basic Mass Tags of this invention and a cation exchange resin for purification of labelled analyte molecules.

In preferred embodiments the kit may additionally comprise reaction buffers for the coupling of the tag to analyte molecules, buffers for washing of the cation exchange resin after the reaction buffer has been loaded onto the resin and buffers for elution of the labelled peptides from the resin after the unreacted tags have been washed away. A preferred wash buffer comprises water and acetonitrile at a low pH while a preferred elution buffer comprises ammonium acetate. In preferred embodiments the reaction buffer comprises borate, urea and thiourea. Preferably, the urea and thiourea are present at a combined concentration of at least 1M.

The invention will now be described in more detail by way of example only, with reference to the figures, in which.

MKWVTFISLLLLFSSAYSRGVFRRDTHKSEIAHRFKDLGEEHFKGLVLIA

FSQYLQQCPFDEHVKLVNELTEFAKTCVADESHAGCEKSLHTLFGDELCK

VASLRETYGDMADCCEKQEPERNECFLSHKDDSPDLPKLKPDPNTLCDEF

KADEKKFWGKYLYEIARRHPYFYAPELLYYANKYNGVFQECCQAEDKGAC

LLPKIETMREKVLASSARQRLRCASIQKFGERALKAWSVARLSQKFPKAE

FVEVTKLVTDLTKVHKECCHGDLLECADDRADLAKYICDNQDTISSKLKE

CCDKPLLEKSHCIAEVEKDAIPENLPPLTADFAEDKDVCKNYQEAKDAFL

GSFLYEYSRRHPEYAVSVLLRLAKEYEATLEECCAKDDPHACYSTVFDKL

KHLVDEPQNLIKQNCDQFEKLGEYGFQNALIVRYTRKVPQVSTPTLVEVS

RSLGKVGTRCCTKPESERMPCTEDYLSLILNRLCVLHEKTPVSEKVTKCC

TESLVNRRPCFSALTPDETYVPKAFDEKLFTFHADICTLPDTEKQIKKQT

ALVELLKHKPKATEEQLKTVMENFVAFVDKCCAADDKEACFAVEGPKLVV

Figure 4:
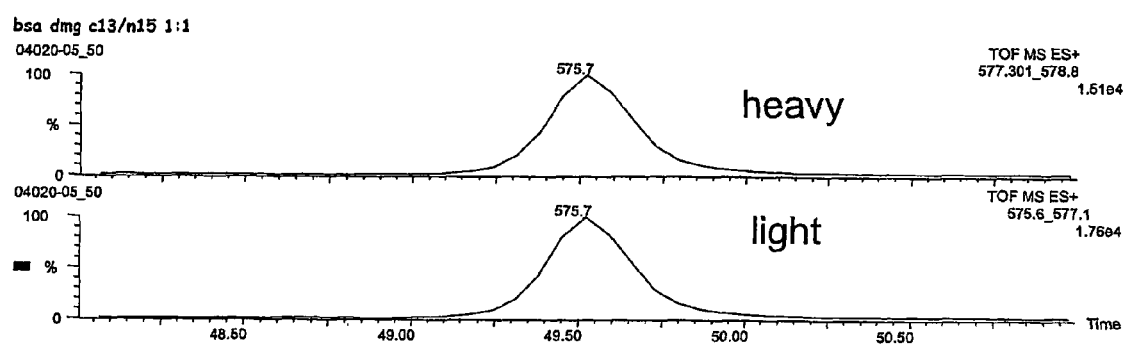
Figure 5:
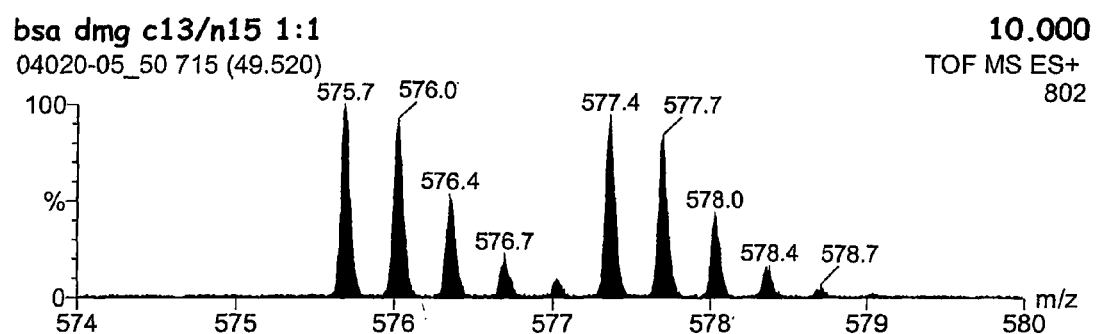
Figure 6:
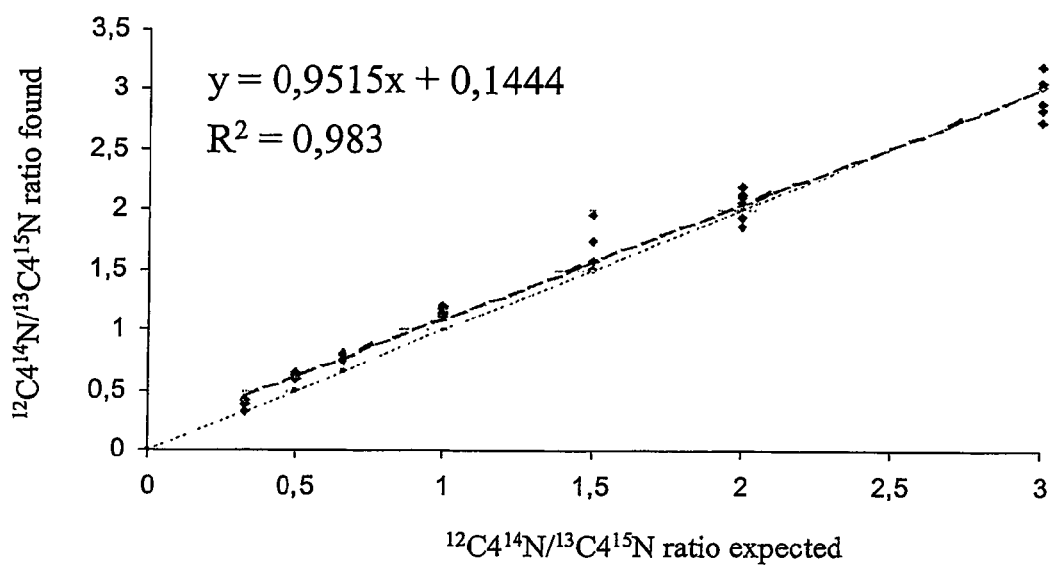

STQTALA;

FIG. 4 shows a study of elution time for a differentially labelled peptide pair, K*VPQVSTPTLVEVSR (SEQ ID NO: 2), where * are the stable isotopes DMG $^{13}C_4{}^{15}N$ (heavy) or DMG $^{12}C_4{}^{14}N$ (light), highlighting the accurate coelution of the labelled peptide pairs;

FIG. 5 shows quantification using $^{12}C/^{13}C^{15}N$ DMG labels for the differentially labelled peptide, K*VPQVSTPTLVEVSR (SEQ ID NO: 2), highlighting the effective discrimination of the two isotope patterns due to the 5 amu differential arising from the $^{12}C/^{13}C^{15}N$ DMG labels, and also highlighting the effectiveness of the mass difference between the patterns for allowing quantitative analysis; and FIG. 6 demonstrates the accuracy of the quantitative analysis using $^{12}C/^{13}C_4{}^{15}N$ DMG labels; the analysis was performed on 3 peptides having the following labelling characteristics:

7 different ratios of DMG $^{12}C_4{}^{14}N$ and DMG $^{13}C_4{}^{15}N$ labelling, (1/3; 1/2; 2/3; 1/1; 2/1; 3/2; and 3/1)
differing numbers of labels
different size and charge states as follows:

```
(DMG)PCTEDYLSLILNR      (SEQ ID NO: 3)    (2+ and 3+)

K(DMG)VPQVSTPTLVEVSR    (SEQ ID NO: 2)    (2+ and 3+)

(DMG)AALK(DMG)AWSVAR    (SEQ ID NO: 4)    (2+ and 3+)
```

The graph of this Figure plots a regression line for 7 different expected and observed ratios of the above 3 peptides.

Tertiary Amino Groups

The Basic Mass Tag reagents of the first aspect of this invention comprise a tertiary amino group linked to an amine-reactive functionality. The purpose of these reagents is to protect primary amino groups in natural or synthetic biomolecules, particularly proteins, while retaining a functionality that can still protonate, which is advantageous for purification of labelled biomolecules and is also advantageous for analysis of the labelled biomolecules by mass spectrometry, particularly for ionisation techniques that primarily rely on protonation for ionisation of analytes such as Electrospray Ionisation and MALDI TOF. Tertiary amines readily protonate but do not readily participate in nucleophilic attack on electrophiles. The substituents to the nitrogen in a tertiary amino group can be easily modified to allow the accessibility of the nitrogen to be altered and to alter the proton affinity of the nitrogen.

Tertiary amines are advantageous for the labelling of peptides as they retain a 'mobile' proton which facilitates sequencing of peptides by collision induced dissociation of the peptides (Schlosser and Lehmann 2000; Wysocki, Tsaprailis et al. 2000). Thus the tags of this invention provide a protecting group that allows the labelled peptide to behave in a manner similar to the unlabelled species when analysed by mass spectrometry.

Similarly, with the preferred compounds of this invention only a very small change in retention times is noticed when comparing the chromatographic separation of the labelled peptides and the unlabelled peptides.

For the purposes of this invention methyl groups are sufficient to protect the nitrogen when it is connected to a reactive functionality via a linear alkyl chain. N,N-Dimethyl glycine, for example is a good reagent for the preparation of active esters. The N-hydroxysuccinimide ester of this compound is a preferred tag provided by this invention. More hindered substituents are also applicable but very large substituents are not preferred as these will interfere with the chromatographic properties of labelled biomolecules.

Reactive Tags Comprising Tertiary Amino Functionalities

In the first aspect of this invention reactive tertiary amino group containing molecules are provided. Such reagents can be prepared from a number of commercially available intermediates. A number of compounds in which tertiary amino groups are linked to carboxylic acid functionalities, are commercially available (see 'Examples' section below). The carboxylic acid functionality may be readily converted to an active ester or acid chloride by conventional chemical methods (see for example Solomons, "Organic Chemistry", Fifth Edition published by Wiley). Preferred active esters include N-hydroxysuccinimide (NHS) esters and pentafluorophenyl esters.

Reactive Functionalities

A variety of other reactive functionalities may be appropriate to prepare reactive tertiary amino-containing reagents for use with this invention. Table 1 below lists some reactive functionalities that may be incorporated into the reagents of this invention. These reactive functionalities may be reacted with amino groups in natural or synthetic biomolecules, particularly in peptides and polypeptides. Reaction of the reactive functionalities with the nucleophilic functionalities shown generates a covalent linkage between the two entities. This covalent linkage is shown in the third column of the table. For applications involving synthetic oligonucleotides, primary amines are often introduced during the synthesis at the termini of the molecules to permit labelling. Any of the functionalities listed below could be introduced into the compounds of this invention to permit the mass markers to be attached to a molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
| --- | --- | --- |
| —$NH_2$ | —$SO_2$—CH=$CR_2$ | —N($CR_2$—$CH_2$—$SO_2$—$)_2$ or —NH—$CR_2$—$CH_2$—$SO_2$— |
| —$NH_2$ | —CO—X | —CO—NH— |
| —$NH_2$ | —CO—O—CO— | —CO—NH— |
| —$NH_2$ | (NHS ester) | —CO—NH— |
| —$NH_2$ | (HOBt ester) | —CO—NH— |
| —$NH_2$ | —NCO | —NH—CO—NH— |
| —$NH_2$ | —NCS | —NH—CS—NH— |
| —$NH_2$ | —CHO | —$CH_2$—NH— |
| —$NH_2$ | —$SO_2$—X | —$SO_2$—NH— |
| —$NH_2$ | $CH_2$=CH— | —NH—$CH_2$—$CH_2$— |

It should be noted that in applications involving labelling oligonucleotides with the mass markers of this invention, some of the reactive functionalities above or their resultant linking groups might have to be protected prior to introduction into an oligonucleotide synthesiser. Preferably unprotected ester, thioether and thioesters, amine and amide bonds are to be avoided, as these are not usually stable in an oligonucleotide synthesiser. A wide variety of protective groups is known in the art which can be used to protect linkages from unwanted side reactions. Alternatively, amine functionalised oligonucleotides can be prepared using standard methods known in the art and these can be labelled with amine reactive reagents such as NHS-esters.

Basic Mass Tags with Characteristic Isotope Abundance Distributions

While peptides have characteristic isotope abundance distributions, it is often worthwhile to modify the isotope abundance distributions of peptides to allow specific features to be identified. One way of identifying cysteine containing peptides is to tag the cysteines with a label that gives the peptides a characteristic isotope distribution. A number of labels and tagging procedures have been developed for this purpose (Sechi and Chait 1998; Adamczyk, Gebler et al. 1999; Goodlett, Bruce et al. 2000; Sechi 2002).

In a typical analysis of a complex peptide mixture, the peptides are separated by HPLC, for example, and the eluting material is sprayed directly into a mass spectrometer through an ESI interface for analysis. Usually peptides are identified by MS/MS in an appropriate instrument. Since identification of peptides by MS/MS is moderately time-consuming, the speed of this type of analysis determines the overall throughput of the instrument for identification of peptides in samples. In instruments such as Quadrupole/Time-of-Flight machines in which MS-mode acquisition of spectra is comparatively rapid, the MS-mode can be used to identify ions as they are generated to determine which species to analysis by MS/MS . However, with unmodified peptides, it is sometimes difficult to distinguish between peptide ions and non-peptide contaminants in the MS-mode. This means that ions that are not peptides are often selected for MS/MS analysis, reducing the overall throughput of the instrument for peptide identification. To overcome this problem, this invention provides tags for the labelling of amino groups in polypeptides and peptides that alter the isotope abundance distribution of polypeptides and peptides. Since most peptides or polypeptides have at least one amino group this provides a way of tagging polypeptides or peptides to allow their ions to be distinguished from other ions present in the MS-mode by the modified isotope abundance distributions of the labelled peptides. This is advantageous as it ensures that time is not wasted analysing ions by CID that are not peptides. Thus in preferred embodiments of the first aspect of this invention, BMT reagents with characteristic isotope distributions are provided. When used to label a peptide or polypeptide these tags will modify the isotope distribution of the labelled species. In one embodiment, a characteristic isotope distribution can be imparted to tags of this invention by incorporation of one or more halogen atoms into the tag, generally substituting for hydrogen atoms. Both bromine (Steen and Mann 2002) and chlorine (Goodlett, Bruce et al. 2000) have been used for this purpose in the prior art and would be appropriate. These atoms will increase the intensity of higher mass isotope peaks when compared to corresponding hydrogenated species. Similarly, fluorine will alter the isotope distribution of a tagged species as it is known to comprise almost exclusively a single isotope, so higher mass isotopes will be of reduced intensity when compared with the corresponding hydrogenated species. Halogen atoms will also introduce a mass defect (Steen and Mann 2002) into the tags which provides a further means for identifying tagged peptides.

It has been previously shown that a reagent for the labelling of cysteine that imparts a characteristic isotope distribution can be prepared from a mixture of compounds comprising natural and isotope enriched species of the same molecule (Adamczyk, Gebler et al. 1999). In a further embodiment, a tag reagent comprising a mixture of BMT reagent isotopes is provided. It is possible to obtain isotope enriched compounds for the synthesis of tags enriched for particular atomic species. For the purpose of illustration consider the tags provided in the 'Examples' section below, in which bromoacetic acid is used as one of the building blocks of a number of reagents. It is possible to obtain 99% $^{13}C$-enriched bromoacetic acid ($Br^{13}CH_2^{13}COOH$) from Aldrich (Sigma-Aldrich Chemie GmbH, Eschenstrasse 5, 82024, Taufkirchen, Germany). It would, therefore, be trivial to introduce this reagent into the synthetic procedures described below. This tag would have a characteristic isotope abundance distribution itself but it would also be possible to mix this reagent with the corresponding reagent synthesized from bromoacetic acid comprising a natural isotope abundance. Different ratios of the two tags would allow tags with controlled isotope abundance distributions to be generated.

Further Labelling of Cleavage Peptides Generated from BMT Labelled Proteins

In the second aspect of this invention, a BMT labelled polypeptide is cleaved with a sequence specific cleavage reagent and the cleavage peptides are analysed by mass spectrometry. In preferred embodiments of this aspect of the invention, the cleavage peptides are labelled further on the amino groups exposed by the cleavage of the peptides. Since the labelling of the polypeptide will have blocked all other free amino groups, only the newly exposed amino groups at the N-termini of the cleavage peptides will be available. Furthermore, the N-terminal peptide of the parent polypeptide will have no free amino group after cleavage as this will have been blocked with the BMT reagent of this invention.

This provides a means of distinguishing the N-terminal fragment of the parent polypeptide from the non-N-terminal peptides. In one embodiment, the non-N-terminal fragments can be labelled by biotinylation with an amine-reactive biotin reagent such as N-hydroxysuccinimide biotin, which is commercially available (Pierce UK Ltd. Chester, UK or Sigma-Aldrich, Poole, Dorset, UK), and captured onto an avidinated support allowing the N-terminal peptide to isolated. Alternatively, the alpha-amino groups of the non-N-terminal peptides can be reacted with a primary-amine reactive solid support leaving the N-terminal peptide in solution.

In an alternative embodiment, the BMT labelled cleavage peptides can be labelled with an amine-reactive biotin reagent to allow the peptides to be captured onto an avidinated support for conditioning of the peptides prior to analysis by mass spectrometry. Conditioning of the peptides means washing of the peptides with a volatile buffer to remove metals ions, detergent and other reagents that were used in the isolation and labelling of the parent polypeptide.

In a further embodiment, the cleavage peptides can be labelled with a further tag such as those disclosed in WO 01/68664 and PCT/GB02/04240, which disclose organic molecule mass markers that are analysed by MS/MS. These applications disclose two component mass markers connected by a collision cleavable group. Sets of tags are synthesised where the sum of the masses of the two components produces markers with the same overall mass. The mass markers may be analysed after cleavage from their analyte or may be detected while attached to the analyte. In the context of this invention the mass markers are detected while attached to the peptide that they are identifying. Selection of the mass of the mass marker with its associated peptide by the first mass analyser of a tandem instrument allows the marked peptides to be abstracted from the background. Collision of the markers in the second stage of the instrument separates the two components of the tag from each other. Only one of these components is detected in the third mass analyser. This allows confirmation that the peak selected in the first analyser is a mass marked peptide. The whole process greatly enhances the signal to noise ratio of the analysis and improves sensitivity. This mass marker design also compresses the mass range over which an array of mass markers is spread. Moreover, it allows the design of markers, which are chemically identical, have the same mass but which are still resolvable by mass spectrometry. This is essential for analytical techniques such as Liquid Chromatography Mass Spectrometry (LC-MS) where the effect of different markers on the mobility of different samples of peptides must be minimised so that corresponding peptides from each sample elute together into the mass spectrometer, allowing the ratios of the corresponding peptides to be determined. These markers are thus most preferred for the purposes of this invention because of the use of high selectivity detection and the closely related structures of these markers. Other markers may also be applicable, though.

Proteins contain various nucleophilic functionalities, besides amino groups, that can be labelled using reagents that are reactive to these functionalities. Proteins typically contain thiol, amino, hydroxyl and imidazole groups. These may all be labelled with appropriate reagents if desired. In preferred embodiments of this invention, thiol groups are labelled prior to labelling of free amino groups. Numerous methods for selective labelling of thiols are known in the art, although preferred reagents include iodoacetamide, vinylpyridine, phenyl vinyl sulphone and maleimide compounds.

Analysis of Labelled Biomolecules

In the second aspect of this invention, a method of analysing polypeptides is provided. In this method the biomolecules are covalently labelled with a reactive tertiary amino group containing compound.

A polypeptide or peptide or mixtures of polypeptides or peptides can be isolated for analysis by any of the conventional means such as electrophoresis, chromatography or affinity chromatography. For the purposes of mass spectrometry, particularly MALDI TOF mass spectrometry, it is preferred that polypeptides or proteins are not contaminated with salts or detergents, particularly metal salts. Various techniques for 'desalting' a polypeptide or peptide mixture are known in the art such as gel filtration, dialysis or the use of hydrophobic resins. A particularly convenient and simple method for de-salting peptides involves aspiration of a small quantity of a solution of the peptide or polypeptide mixture in a pipette tip incorporating C18 packing materials. Hydrophobic material, such as salts and detergents have only a weak affinity for the C18 derivatives and are easily washed through while peptides adhere to the C18 matrix. The captured peptide material can be subsequently eluted with an appropriate volatile buffer for analysis. This sort of 'sample conditioning' substantially improves the detection sensitivity of the analysis of the peptides. Pipette tips pre-packaged with appropriate resins and instructions for their use are commercially available from Millipore (Bedford, Mass. USA) under the trademark 'Zip Tip'. Desalting procedures may take place after labelling of the analyte to remove unreacted tags, if preferred.

The inventors have also observed that peptides labelled with the tags of this invention have a higher affinity for cation exchange resins, particularly strong cation exchange resins, than the tags alone. This allows peptides labelled with the tags of this invention to be purified from unreacted tags by incubation of the reaction mixture with a cation exchange resin. The labelled peptides adhere to the resin, while the unreacted tag, detergents and chaotropes can be washed away with an acidic aqueous solvent. The labelled peptides can then be eluted with an appropriate buffer. For the purposes of subsequent mass spectrometric analysis, elution with a volatile buffer like ammonium acetate, is effective to recover the peptides in a form that is compatible with the mass spectrometer. Accordingly, it is envisaged that pipette tips, spin columns and cartridges packed with a cation exchange resin will be useful tools for the preparation of labelled samples to allow facile clean-up of the labelled peptides prior to analysis.

Analytical Separation of Tagged Peptides

In preferred embodiments of the second aspect of this invention the tagged peptides generated by cleavage of BMT labelled proteins are subjected to analytical separation prior to analysis by mass spectrometry. Most analytical separation techniques that can be applied to peptides will applicable with this invention, such as Capillary Electrophoresis (Moini 2002), High Performance Liquid Chromatography (Morand, Burt et al. 2001), Capillary Iso-electric Focusing (Tang, Harrata et al. 1997; Shen, Berger et al. 2000), Ion Exchange Chromatography and Size Exclusion Chromatography (Liu, Lin et al. 2002).

In more preferred embodiments multidimensional chromatography (Washburn, Wolters et al. 2001; Wolters, Washburn et al. 2001; Liu, Lin et al. 2002) is applied to the tagged peptides generated by cleavage of BMT labelled proteins.

Quantitative Analysis of Tagged Peptides

The present invention further provides a method for characterising molecules in which a plurality of molecules are characterised by mass spectrometry, wherein the characterisation includes determination of the quantity present of at least one of the molecules, or relative quantities present of two or more of the molecules.

In this method, it is preferred that each of the plurality of molecules to be analysed is labelled with a differentially isotopically labelled mass tag reagent of the present invention, such that both the identity and quantity of each molecule may be determined by mass spectrometry. In these embodiments of the present invention, it is particularly preferred that the mass tag reagent comprises a DMG mass tag reagent.

Using the methods and tags of the present invention, mass spectra can be obtained of sufficiently high quality that integration of the spectrum can give reliable data on the quantities of the species that are present. An example of this procedure is provided below, and a sample spectrum can be seen in FIG. 5 for a 2-component analysis using differentially isotopically labelled DMG tags.

Isotopic labelling lends itself particularly well to these analyses, since the chemical structure of the tags is identical, and will lead to identical mass spectral ion patterns, each pattern being displaced from the other by virtue of the mass difference resulting from the isotopic labelling. This mass difference can be controlled by changing the degree of isotopic labelling in the tags. Since the patterns are identical, then they may be more easily compared and integrated, allowing a more accurate comparison and determination of relative quantities.

Absolute quantities may also be determined by comparing the mass spectrum data with a control having a known quantity.

Mass Spectrometry of Tagged Peptides

The essential features of a mass spectrometer are as follows:

Inlet System->Ion Source->Mass Analyser->Ion Detector->Data Capture System

There are various inlet systems, ion sources and mass analysers that can be used for the purposes of analysing large biomolecules but in the context of this invention the ion source is preferably and Electrospray Ionisation (ESI) source or a Matrix Assisted Laser Desorption Ionisation (MALDI) source. ESI can be coupled to most types of mass analysers including Ion Traps, Quadrupole and Triple Quadrupole instruments, orthogonal axis Time-of-Flight and Quadrupole/Time-of-flight mass analysers. Similarly, a variety of mass analysers, ion detectors and data capture systems may be used with MALDI although some mass spectrometer geometries are not commercially produced. Time-of-flight mass analysers are typically used with MALDI as well as Fourier Transform Ion Cyclotron Resonance mass analysers and Quadrupole/Time-of-flight mass analysers. In principle ion traps and sector instruments can also be used with MALDI but generally these are not widely available.

Electrospray Ionisation

Electrospray ionisation requires that a dilute solution of the analyte molecule is 'atomised' into the spectrometer, i.e. injected as a fine spray. The solution is typically sprayed from the tip of a charged needle in a stream of dry nitrogen and an electrostatic field. The mechanism of ionisation is not fully understood but is thought to work broadly as follows. In a stream of nitrogen the solvent is evaporated. With a small droplet, this results in concentration of the analyte molecule. Given that most biomolecules have a net charge this increases the electrostatic repulsion of the dissolved molecule. As evaporation continues this repulsion ultimately becomes greater than the surface tension of the droplet and the droplet disintegrates into smaller droplets.

This process is sometimes referred to as a 'Coulombic explosion'. The electrostatic field helps to further overcome the surface tension of the droplets and assists in the spraying process. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to accelerate ions from the ionisation chamber it is possible to control the fragmentation of ions. This is advantageous when fragmentation of ions is to be used as a means of removing tags from a labelled biomolecule.

Matrix Assisted Laser Desorption Ionisation (MALDI)

MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Proton transfer from the acidic matrix to the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. Accelerating voltages can again be used to control fragmentation with this technique though. This technique is highly favoured for the determination of peptide mass fingerprints due to its large mass range, due to the prevalence of singly charged ions in its spectra and due to the ability to analyse multiple peptides simultaneously.

The photo-excitable matrix comprises a 'dye', i.e. a compound that strongly absorbs light of a particular frequency, and which preferably does not radiate that energy by fluorescence or phosphorescence but rather dissipates the energy thermally, i.e. through vibrational modes. It is the vibration of the matrix caused by laser excitation that results in rapid sublimation of the dye which simultaneously takes the embedded analyte into the gas phase.

Mass Analysers

Time-of-Flight Mass Analysers

As the name implies, Time-of-flight mass analysers measure the time it takes for ions to travel a predetermined distance under the influence of a predetermined potential difference. The time-of-flight measurement allows the mass-to-charge ratio of ions striking a detector to be calculated. These instruments measure the arrival of almost all of the ions in a sample and as a result can be quite sensitive although, selectivity with this technique is more difficult to achieve. This technique can also detect ions wither high mass-to-charge ratios than can be typically measured in an ion trap or quadrupole mass spectrometer. TOF mass analysers are presently widely used with MALDI.

Ion Traps

Ion Trap mass analysers are related to the quadrupole mass analysers. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device as the ions entering the trap are essentially cooled to the ambient temperature of the bath gas through collision with the bath gas. Collisions both increase ionisation when a sample is introduced into the trap and dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole, for example.

Identification of Peptides by Collision Induced Dissociation

In the second aspect of this invention the tagged peptides generated by cleavage of BMT labelled polypeptides are analysed by mass spectrometry. This analysis may include identification of the peptides by mass spectrometry. Various mass analyser geometries may be used to fragment peptides and to determine the mass of the fragments such as ion traps, triple quadrupoles, quadrupole/time-of-flight, time-of-flight/time-of-flight and serial sector instruments.

MS/MS and MS$^n$ Analysis of Peptides:

Tandem mass spectrometers allow ions with a pre-determined mass-to-charge ratio to be selected and fragmented by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are denoted $a_n$, $b_n$, $c_n$, etc. for cleavage at the $n^{th}$ peptide bond where the charge of the ion is retained on the N-terminal fragment of the ion. Similarly, fragment series are denoted $x_n$, $y_n$, $z_n$, etc. where the charge is retained on the C-terminal fragment of the ion.

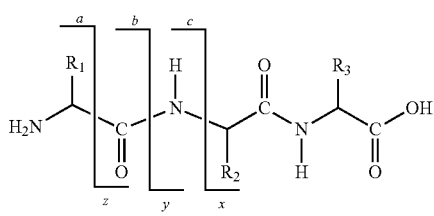

Trypsin, Lys-C and thrombin are favoured cleavage agents for tandem mass spectrometry as they produce peptides with basic groups at both ends of the molecule, i.e. the alpha-amino group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the b-series.

In general peptides fragment via a mechanism that involves protonation of the amide backbone follow by intermolecular nucleophilic attack leading to the formation of a 5-membered oxazolone structure and cleavage of the amide linkage that was protonated (Polce, Ren et al. 2000; Schlosser and Lehmann 2000). This mechanism requires a carbonyl group from an amide bond adjacent to a protonated amide on the N-terminal side of the protonated amide to carry out the nucleophilic attack. A charged oxazolonium ion gives rise to b-series ions, while proton transfer from the N-terminal fragment to the C-terminal fragment gives rise to y-series ions. This requirement for an appropriately located carbonyl group does not account for cleavage at amide bonds adjacent to the N-terminal amino acid, when the N-terminus is not protected and, in general, b-series ions are not seen for the amide between the N-terminal and second amino acid in a peptide. However, peptides with acetylated N-termini do meet the structural requirements of this mechanism and fragmentation can take place at the amide bond immediately after the first amino acid by this mechanism. Peptides labelled on lysine or at an alpha-amino group with active ester tags of this invention should not undergo significant cleavage at the tag peptide during low energy CID analysis if there is no appropriately located carbonyl group in the tag molecule. This means that CID spectra for labelled peptides should be similar to the spectra for unlabeled peptides although the spectra will show mass shifts corresponding to multiples of the mass of the tag. This can be readily compensated for in the analysis of such CID spectra.

Similarly, peptides can be identified in single Time-of-Flight (TOF) mass analysers by a process referred to as Post-Source Decay (PSD) (Kaufmann, Chaurand et al. 1996). This is particularly effective in TOF mass analysers equipped with Delayed Extraction ion optics. MALDI tends to impart a high level of kinetic energy to analyte molecules that can cause fragmentation of the ions which can be used to deduce the sequence of the parent peptide ion.

The following examples illustrate some of the features and possible embodiments of the invention but other embodiments are envisaged.

EXAMPLES

1. Syntheses of Basic Mass Tags

All reagents were obtained from Aldrich (Sigma-Aldrich Chemie GmbH, Eschenstrasse 5, 82024, Taufkirchen, Germany).

Basic Mass Tags were synthesised by activation of the corresponding carboxylic acid forms of the compounds to give the N-hydroxysuccinimide esters by standard methods. The reagents N,N-dimethylglycine, N,N-3-amninobutyric acid are commercially available.

DIG, PAA, MAA and DMA were prepared by reaction of diisopropylamine, piperidine, morpholine and dimethylpiperidine with a bromoacetic acid ester, respectively, to give the corresponding acetic acid ester derivatives, which were then deprotected to give the free carboxylic acids for activation. Detailed protocols are listed below:

Diisopropylamino-acetic acid-tert.butylester 2

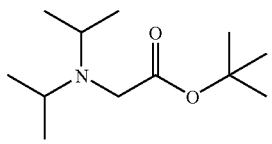

2

5.85 g (30 mMol) Bromoacetic acid-tert.butylester and 9.9 ml (70 mMol) diisopropylamine were stirred for 5-7 h under reflux in 50 ml THF. After removing the solvents, the product was dissolved in water and the pH of the solution was adjusted to pH 11 with 2 N NaOH. The heterogeneous reaction mixture was extracted with EtOAc, washed with water and dried (sodium sulphate). The residue, after evaporation of the solvent was eluted from a silica gel column with dichloromethane/methanol (10/1 v/v).

yield: 5.4 g (84%)
$R_F$=0.54 ($CH_2Cl_2/CH_3OH$=5:1)
$^1$H-NMR (CDCl$_3$) δ 0.98 (d, 12H, iProp-CH$_3$), 1.42 (s, 9H, tert-Bu); 3.04 (m, 2H, iProp-CH); 3.07 (s, 2H, N—CH$_2$).

Diisopropylamino-acetic acid hydrochloride 3

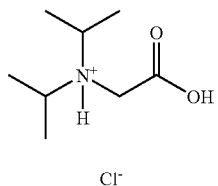

3

5.4 g (25 mMol) diisopropylamino-acetic acid tert-butylester 2 was stirred with 6.25 ml (75 mMol) 12 M HCl in 25 ml water for 2.5 h at 60° C. After distillation in vacuo of water and excess of HCl, the residue was dried with toluene azeotropically.

Yield: 4.1 g (84%)
$^1$H-NMR (d$_6$-DMSO) δ 1.24 (d, 12H, iProp-CH$_3$); 3.66 (m, 2H, iProp-CH); 4.08 (s, 2H, N—CH$_2$); 8.6 (br.s, 2H, N$^+$H, OH)

Diisopropylamino-acetic acid-(2,5-dioxo-pyrrolidine-1-yl)-ester 4

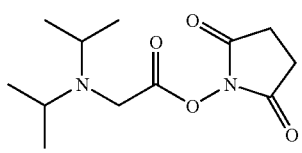

4

3.82 g (19.5 mMol) diisopropylamino-acetic acid hydrochloride (3), in 50 ml DMF, was added to 2.24 g (19.5 mMol) N-hydroxysuccinimide and 8.04 g (39 nMol) dicyclohexylcarbodiimide. The reaction mixture was stirred for 16 h at RT. The residue was filtered and the filtrate was evaporated in vacuum to dryness. After dissolving the residue in CH$_2$Cl$_2$, the solution was washed with NaHCO$_3$, dried (sodium sulphate) and the solvent evaporated. The compound was then recrystallised from diisopropylether.

Yield: 3.5 g (70%)
Mp. 96° C.
$^1$H-NMR (CDCl$_3$) δ 1.04 (d, 12H, iProp-CH$_3$), 2.81 (s, 4H, O-Su); 3.11 (m, 2H, iProp-CH); 3.59 (s, 2H, N—CH$_2$)

(2,6-Dimethyl-piperidine-1-yl)-acetic acid tert-butylester 5

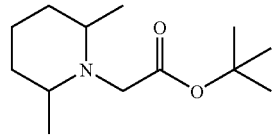

5

14.8 ml (100 mMol) bromoacetic acid tert-butylester 1 and 29.9 ml (230 mMol) 2,6-dimethyl-piperidine were stirred for 5 h at reflux in 150 ml THF. After removing the solvents, the product was dissolved in water and the pH of the solution was altered to pH 11 with 2 N NaOH. The heterogeneous reaction mixture was extracted with EtOAc, washed with water and dried (sodium sulphate). The residue, after evaporation of the solvent, was eluted from a silica gel column with diisopropylether Yield: 21.6 g (95%)
$R_F$=0.58 (diisopropylether)
1H-NMR (CDCl$_3$) δ 1.09 (d, 6H, 2x N—C—CH$_3$), 1.16-1.67 (m, 6H, Pip-CH$_2$—CH$_2$—CH$_2$); 1.43 (s, 9H, tert-Bu); 2.81 (m, 2H, 2x N—CH); 3,45 (s, 2H, N—CH$_2$)

(2,6-Dimethyl-piperidine-1-yl)-acetic acid hydrochloride 6

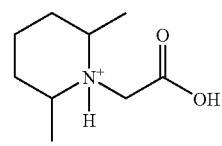

6

21.6 g (95 mMol) (2,6-dimethyl-piperidine-1-yl)-acetic acid tert-butylester (5) was stirred with 23.75 ml (285 mmol) 12 M HCl in 100 ml water for 2 h at 60° C. After distillation in vacuo of water and excess of HCl, the residue was dried with toluene azeotropically.

Yield: 19.5 g (>98%)
$R_F$=0.18 (CH$_2$Cl$_2$/CH$_3$OH=5:1)

¹H-NMR (d₆-DMSO) δ 1.1-1.38 (m, 6H); 1.4-1.9 (m, 6H); 3.35-3.65 (m, 2H); 405 (s, 2H); 9.05 (br.s, 1H); 10.85 (s, 1H)

(2,6-Dimethyl-piperidine-1-yl)-acetic acid-(2,5-dioxo-pyrrolidine-1-yl)-ester 7

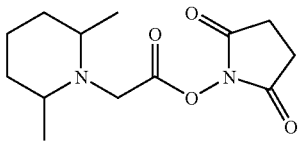

4.15 g (20 mMol) (2,6-dimethyl-piperidin-1-yl)-acetic acid hydrochloride (6), in 50 ml DMF, was added to 2.3 g (20 mMol) N-hydroxysuccinimide and 8.1 g (40 mMol) dicyclohexylcarbodiimide. The reaction mixture was stirred for 16 h at RT. The residue was filtered and the filtrate was evaporated under vacuum to dryness. After dissolving the residue in CH₂Cl₂, the solution was washed with NaHCO₃, dried (sodium sulphate) and the solvent evaporated. The compound was then recrystallised from diisopropylether (A-Kohle).

Yield: 3.7 g (69%)

Mp 72° C.

¹H-NMR (CDCl₃) δ 1.14 (d, 6H, 2x N—C—CH₃), 1.18-1.7 (m, 6H, Pip-CH₂—CH₂—CH₂); 2.75-2.85 (m, 2H, 2x N—CH); 2.82 (s, 4H, O-Su); 3.9 (s, 2H, N—CH₂)

(Piperidine-1-yl)-acetic acid-benzylester 9

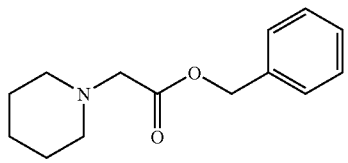

11.45 g (50 mMol) bromoacetic acid-benzylester 8 was carefully added to 9.36 g (110 mMol) piperidine in 100 ml THF. The reaction mixture was stirred for 4 h at reflux. After distillation of THF, the residue was solved in CH₂Cl₂/H₂O and the pH of the solution was adjusted to pH 10.5 with 2 N NaOH. The product was then extracted in CH₂Cl₂ and dried over sodium sulphate. After evaporation of the solvent, the product was subjected to a chromatographic purification using ethyl acetate.

Yield: 10.4 g (89%)

R_F=0.67 (EtOAc)

HPLC: >97% [ET 250/8/4 Nucleosil 7 μm phenyl Machery & Nagel # 720019; Acetonitrile: (H₂O+0.01 M TBAS)=95:5; flow 1 ml/Min.; 5.3 min.]

¹H-NMR (CDCl₃) δ 1.42 (m, 2H, C—C—CH₂—C—C); 1,57-1.62 (m, 4H, C—CH₂—C—CH₂—C); 2.49 (t, 4H, CH₂—N—CH₂); 3.21 (s, 2H, N—CH₂—CO); 5.14 (s, 2H, O—CH₂); 7.28-7.33 (m, 5H, Ph)

(Piperidine-1-yl)-acetic acid 10

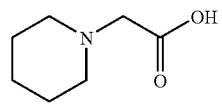

10.4 g (44 mMol) (piperidine-1-yl)-acetic acid-benzylester 9 was stirred with 0.25 g Pd/C (5%) in 100 ml Methanol at RT. Under normal pressure, the reaction mixture was reduced (hydrated) with H₂. After having removed the catalyst, the solution was evaporated and the residue was resuspended in EtOAc and filtered off.

Yield: 6 g (95%)

Mp 231° C.

¹H-NMR (d₆-DMSO) δ 1.45 (m, 2H, C—C—CH₂—C—C); 1.62-1.67 (m, 4H, C—CH₂—C—CH₂—C); 2.89 (t, 4H, CH₂—N—CH₂); 3.19 (s, 2H, N—CH₂—CO); 4-6 (1H, OH)

(Piperidine-1-yl)-acetic acid-(2,5-dioxo-pyrrolidine-1-yl)-ester 11

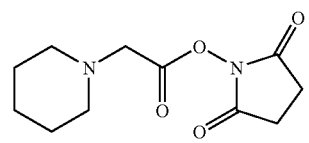

6 g (42 mMol) (piperidine-1-yl)-acetic acid 10 was added to 4.83 g (42 mMol) N-hydroxysuccinimide and 9.53 g (46.2 mMol) dicylohexyl-carbodiimide in 100 ml CH₂Cl₂. The reaction mixture was stirred for 16 h at RT. The residue was filtered and the filtrate was evaporated in vacuum to dryness. The residue was then dissolved in diethylether and the solution was filtered off. The filtrate was reduced once again and the residue was dissolved in Diisopropylether. After filtration of the solution and evaporation of the solvent, the compound was then recrystallised from diisopropylether.

Yield: 7.1 g (70%)

Mp: 82° C.

¹H-NMR (CDCl₃) δ 1.45 (m, 2H, C—C—CH₂—C—C); 1.58 (m, 4H, C—CH₂—C—CH₂—C); 2.6 (t, 4H, CH₂—N—CH₂); 2.84 (s, 4H, CO—CH₂—CH₂—CO); 3.54 (s, 2H, N—CH₂—CO)

(Morpholine-1-yl)-acetic acid-benzylester 12

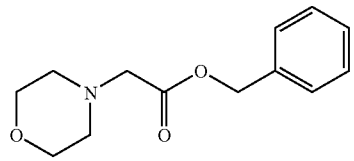

11.45 g (50 Mol) bromoacetic acid-benzylester 8 was carefully added to 9.58 g (110 mMol) morpholine in 100 ml THF. The reaction mixture was stirred for 4 h under reflux. After distillation of THF, the residue was solved in $CH_2Cl_2/H_2O$ and the pH of the solution was altered to pH 10.5 with 2N NaOH. The product was then extracted in $CH_2Cl_2$ and dried over sodium sulphate. After evaporation of the solvent, the product was purified by chromatography using ethyl acetate.

Yield: 11 g (93.5%)

$R_F$=0.63 (EtOAc)

HPLC: >97% [ET 250/8/4 Nucleosil 7 μm phenyl Machery & Nagel # 720019; acetonitrile: (water+0.01 M TBAS)=95:5; flow 1 ml/min.; 4.0 Min.]

$^1$H-NMR (CDCl$_3$) δ 2.56 (t, 4H, CH$_2$—N—CH$_2$); 3.23 (s, 2H, N—CH$_2$—CO); 3.72 (t, 4H, CH$_2$—O—CH$_2$); 5.14 (s, 2H, O—CH$_2$); 7.28-7.33 (m, 5H, Ph)

(Morpholin-1-yl)-acetic acid 13

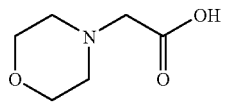

13

11 g (46 mMol) (morpholin-1-yl)-acetic acid benzylester 12 was stirred with 0.25 g Pd/C (5%) in 100 ml Methanol at RT. Under atmospheric pressure, the reaction mixture was hydrogenated with H$_2$. After having removed the catalyst, the solution was evaporated and the residue was resuspended in EtOAc and filtered off.

Yield: 6.3 g (95%)

Mp: 166° C.

$^1$H-NMR (d$_6$-DMSO) δ 2.57 (t, 4H, CH$_2$—N—CH$_2$); 3.14 (s, 2H, N—CH$_2$—CO); 3.58 (t, 4H, CH$_2$—O—CH$_2$); 3.19; 9-12 (1H, OH)

(Morpholine-1-yl)-acetic acid-(2,5-dioxo-pyrrolidine-1-yl)-ester 14

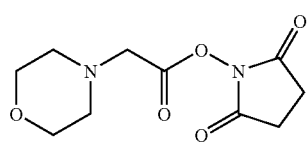

14

6.3 g (44 mMol) (morpholin-1-yl)-acetic acid 13 was added to 5.06 g (44 mMol) N-hydroxysuccinimide and 9.98 g (48.4 mMol) dicylohexyl-carbodiimide in 100 ml CH$_2$Cl$_2$. The reaction mixture was stirred for 16 h at RT. The residue was filtered and the filtrate was evaporated in vacuum to dryness. The residue was then dissolved in Diethylether and the solution was filtered off. The filtrate was reduced once again and the residue was dissolved in Diisopropylether. After filtration of the solution and evaporation of the solvent, the compound was then recrystallized from diisopropylether.

Yield: 8.1 g (76%)

Mp: 142° C.

$^1$H-NMR (CDCl$_3$) δ 2.62 (t, 4H, CH$_2$—N—CH$_2$); 2.8 (s, 4H, CO—CH$_2$—CH$_2$—CO); 3.52 (s, 2H, N—CH$_2$—CO); 3.69 (t, 4H, CH$_2$—O—CH$_2$)

Dimethylamino-acetic acid-(2,5-dioxo-pyrrolidine-1-yl)-ester 16

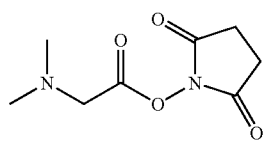

16

5.15 g (50 mMol) Dimethylamino-acetic acid 15 was added to 5.75 g (50 mMol) N-hydroxy-succinimide and 11.05 g (55 mMol) dicyclohexyl-carbodiimide in 100 ml CH$_2$Cl$_2$ at 0° C. The reaction mixture was stirred for 20 h at RT. The residue was filtered and the filtrate was evaporated in vacuum to dryness. The residue was then dissolved in diethylether, mixed with A-Kohle. The solution was filtered off and evaporated. The obtained oil was dissolved in a small amount of diethylether to get a crystallization of the product. The cooled crystal solution was filtered off. The crystals were once again dissolved in Diethylether, treated with A-Kohle and the solution was filtered off. Those purification steps were repeated several times until the obtaining of a pure product in $^1$H-NMR Yield: 0.5-1 g (5-10%)

Mp: 67° C.

$^1$H-NMR (CDCl$_3$) δ 2.42 (s, 6H, 2x CH$_3$); 2.82 (s, 4H, O-Su); 3.52 (s, 2H, N—CH$_2$)

4-Dimethylamino-butyric acid-benzylester 19

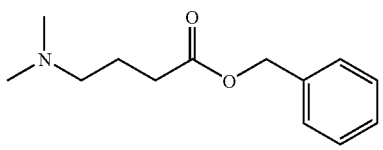

19

25 g (150 mMol) 4-dimethylamino-butyric acid hydrochloride 18, 27.4 g (254 mMol) benzylalcohol and 29.5 g (155 mMol) 4-toluenesulphonic acid monohydrate were stirred in 200 ml toluene at reflux and water was removed by a water separator for ca. 2 h. After cooling the reaction mixture, the toluene phase was extracted 4 times with water. The aqueous phase was then extracted 3 times with EtOAc and the pH of the solution was adjusted to pH 9.5 with NaOH. The product was extracted with ehtylacetate. The organic layer was washed with saturated NaCl solution, dried and evaporated to afford the pure benzylester.

Yield: 30.4 g (92%)

$^1$H-NMR (CDCl$_3$) δ 1.8 (m, 2H, N—C—CH$_2$); 2.17 (s, 6H, 2x CH$_3$); 2.26 (t, 2H, CH$_2$—CO); 2.38 (t, 2H, N—CH$_2$); 5.11 (s, 2H, O—CH$_2$); 7.28-7.37 (m, 5H, Ph)

4-Dimethylamino-butyric acid 20

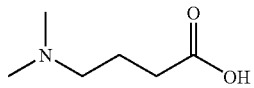

85 g (380 mMol) 4-dimethylamino butyric acid benzylester 19 was stirred with 1 g Pd/C (5%) in 500 ml methanol. The reaction mixture was treated with hydrogen for 4 h. After removing the catalyst, methanol was distilled. A small volume of ethylacetate was added to the remaining residue so that the product would crystallise. The product was then filtered off and washed with ethylacetate.

Yield: 42.5 g (85%)
$^1$H-NMR (d$_6$-DMSO) δ 1.63 (m, 2H, N—C—CH$_2$); 2.22 (s, 6H, 2x CH$_3$); 2.21 (t, 2H, CH$_2$CO); 2.37 (t, 2H, N—CH$_2$); 5.8 (br.s, 1H, OH)

3-Dimethylamino-butyric acid-(2,5-dioxo-pyrrolidine-1-yl)-ester hydrogentosylate 22

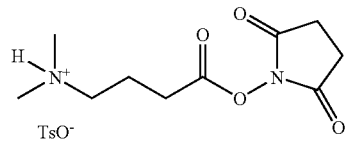

6.55 g (50 mMol) 3-dimethylamino-butyric acid 20 was added to 5.75 g (50 mMol) N-hydroxysuccinimide and 11.05 g (55 mMol) dicyclohexyl carbodiimide in 100 ml CH$_2$Cl$_2$. The reaction mixture was stirred for 16 h at RT. The obtained urea was filtrated and the solution was evaporated. The residue, dissolved in 10 ml acetonitrile, was added under stirring to a solution of 9.51 g (50 mMol) 4-toluenesulfonic acid monohydrate in acetonitrile (30 ml). The solvent was evaporated under vacuum and the product was recrystallized from acetonitrile or acetone.

Yield: 13.8 g (69%)
Mp 133° C.
$^1$H-NMR (d$_6$-DMSO) δ 1.97 (m, 2H, CH$_2$—CO); 2.29 (s, 3H, H$_3$C-Ph), 2.76-2.82 ("m", 12H, 2x CH$_3$, O-Su, C—CH$_2$—C); 3.12 (m, 2H, N—CH$_2$); 7.13 and 7.50 (m, m, 4H, Ph); 9.38 ("s"; 1H, N$^+$H)

3-Dimethylaminobutyric acid-(2,5-dioxo-pyrrolidin-1-yl)-ester hydrogentosylate 22

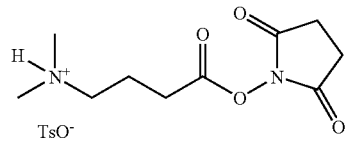

2.62 g (20 mMol) 3-dimethylamino-butyric acid 20 was added to 2.3 g (20 mMol) N-hydroxysuccinimide and 3.8 g (20 Mol) p-toluenesulfonic acid monohydrate and 8.25 g (40 mMol) dicyclohexylcarbodiimide in 100 ml acetonitrile. After stirring the reaction mixture for 16 h at RT, the obtained urea compound was removed and the filtrate evaporated. The residue was recrystallized from acetone.

Yield: 7 g (86%)
Mp 133° C.
$^1$H-NMR (d$_6$-DMSO) δ 1.97 (m, 2H, CH$_2$—CO); 2.29 (s, 3H, H$_3$C-Ph), 2.76-2.82 ("m", 12H, 2x CH$_3$, O-Su, C—CH$_2$—C); 3.12 (m, 2H, N—CH$_2$); 7.13 and 7.50 (m, m, 4H, Ph); 9.38 ("s"; 1H, N$^+$H)

2. Coupling of Basic Mass Tags to beta-MSH 30 nmol βMSH was dissolved in 30 mM BUT (BUT: Buffer of Borate Urea Thiourea), pH 7.5. 30 mM BMT was then added to the peptide solution. After stiring for 2 h, the same amount of BMT was added again and stirred for 2 h. The reaction mixture was then purified with a SCX cartridge to remove the excess of BMTs and the peptide mixture was analysed in LC-MS (LCQ).

3. Labelling of a Test Protein with a Basic Mass Tag

A protocol that is generally applicable to biological samples was used. 500 μg of a commercially available protein, Rabbit Pyruvate Kinase, was first digested with tryspin; 30 μg tryspin (seq. grade modified trypsin, Promega) were added, the pH was adjusted to 7.8 and the solution was incubated at 37° C. for 24 hours. The polypeptide was then dissolved in a BUT buffer (final concentration: Borate 30 mM, 1.5 M urea, 0.7 M thiourea) and reduced with TCEP (1 mM) for 1 h at RT, pH 7.5. After labelling the reduced thiols with iodoacetamide (5 mM), a solution of DMG N-hydroxysuccinimide ester (30 mM final concentration) was added to the reaction mixture and stirred for 4 hours at Room Temperature. The same amount of tag was added a second time and the reaction mixture was stirred at least 4 more hours. To remove the excess of labelling reagents, the guanidine hydrochloride and the DMF and to prepare the sample for MS analysis, the labelled polypeptides sample was purified by an extraction cartridge (HLB Oasis, Waters Corp., Milford, Mass. USA).

4. MS and MS/MS Analysis

Analyses were performed by liquid chromatography mass spectrometry using a Finnigan LCQ Deca with a Finnigan Surveyor HPLC System (Column: Thermo-Hypersil-Keystone BioBasic, 100×1 mm, 5 μm HyPURITY™ Elite C18; Solvents: 100% Water to 100% Methanol both with 0.2% Formic Acid).

Peptide identification was performed by CID (collision of peptide ions selected using 'dynamic exclusion' followed by automatic interpretation of the MS/MS spectra by SEQUEST (Yates, J. R., 3rd; Eng, J. K.; McCormack, A. L., Anal Chem. 67(18) pages 3202-3210, "Mining genomes: correlating tandem mass spectra of modified and unmodified peptides to sequences in nucleotide databases", 1995; MacCoss, M. J.; Wu, C. C.; Yates, J. R., 3$^{rd}$, Anal Chem. 74(21) pages 5593-5599, "Probability-based validation of protein identifications using a modified SEQUEST algorithm", 2002).

Figure 1:
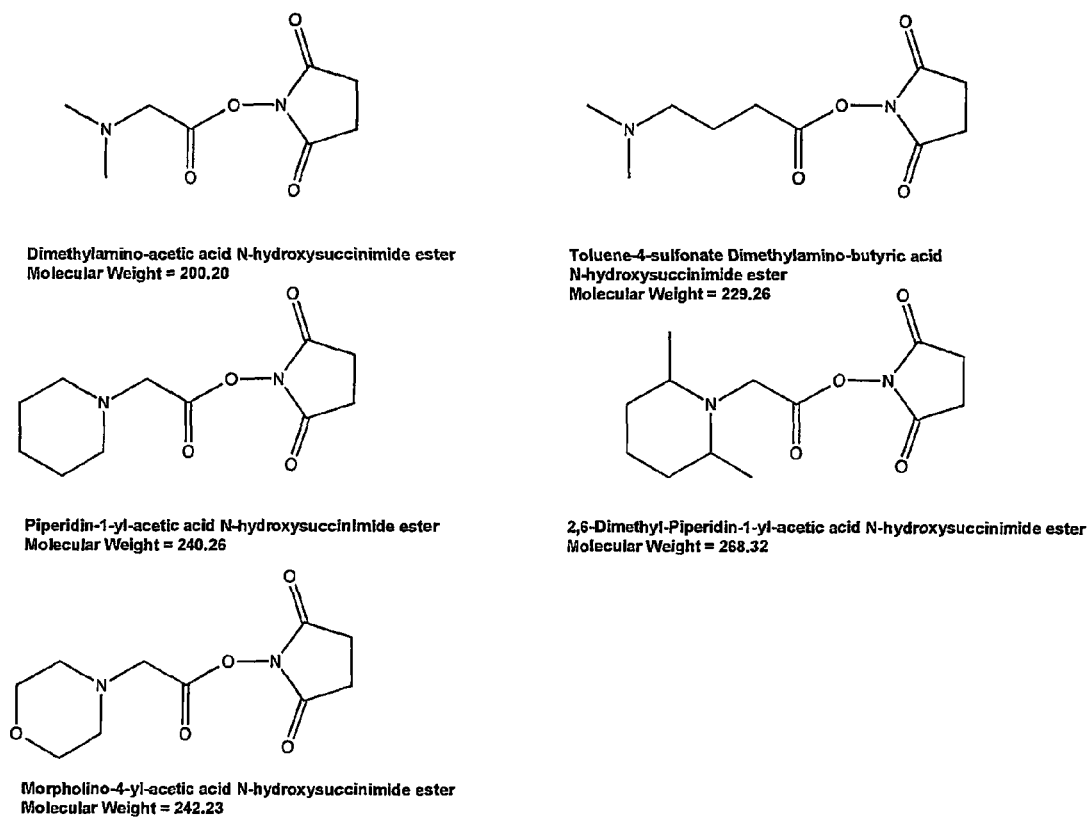
FIG. 1 shows the molecular structures of tags for which synthetic protocols are provided in the 'Examples' section below.
Figure 2:
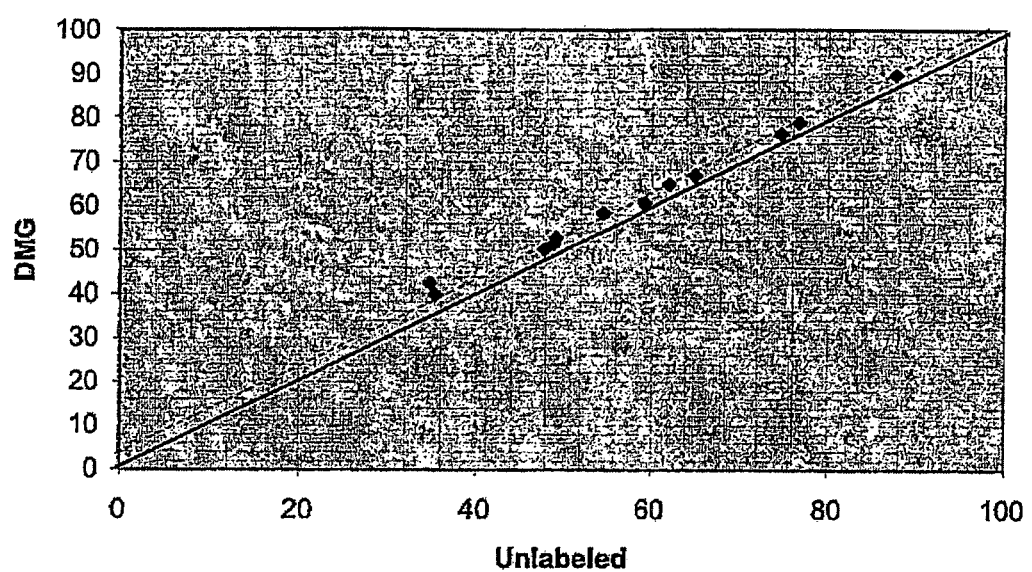
FIG. 2 shows retention times of singly labelled and unlabelled peptides plotted against each other.
Figure 3:
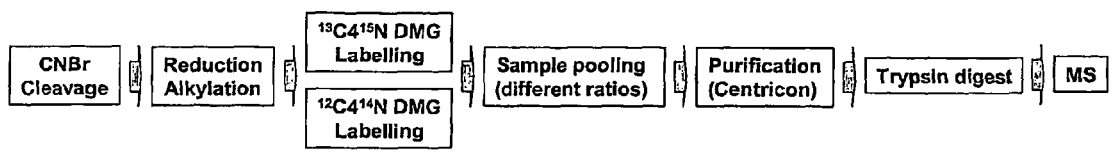
FIG. 3 shows a procedure for a quantification study of a CNBr protein digest using DMG $^{12}C_4{}^{14}N/^{13}C_4{}^{15}N$ isotope labelling —the protein employed was Bovine Albumin (ALB_BOVIN) having a molecular weight of 69293 Da, with the following sequence (SEQ ID NO: 1)

5. Demonstration of Small and Predictable Mobility Shift in Peptides Labelled with DMG The peptides from the tryptic digest of Rabbit Pyruvate Kinase labelled with the N-hydroxysuccinimide active ester of dimethylglycine (DMG) prepared as described was analysed by HPLC-MS/MS with Sequest to identify peptides in parallel with the corresponding analysis of the tryptic digest from the unlabelled Rabbit Pyruvate Kinase. The retention times of singly labelled and unlabelled peptides that were identified in both analyses were recorded and the retention times were plotted against each other in FIG. 2.

Linear regression analysis was performed on this data. When parameters were estimated for the regression it was found that the least squares error was lowest for the intercept that corresponded to a 1.67 minute delay in retention time for a single tag on a peptide when compared with the retention time for the unlabelled peptide. The solid line in FIG. 2 marks where the points would fall if the retention time was the same for labelled and unlabelled peptides, while the broken line marks the regression line. The $R^2$ value for this regression was 0.97 suggesting that it is an accurate model of the effect of the DMG tag on singly labelled peptides.

6. Synthesis of the stable isotope DMG$^{13}C_4, ^{15}N$:
Dimethylamino-acetic acid [$^{13}C_4, ^{15}N$]-(2,5-dioxo-pyrrolidin-1-yl)-ester The starting materials dimethyl $^{13}C_4$-amine-$^{15}N$ HCl (1) and bromoacetic acid-$^{13}C_2$ (2) were obtained by Campro Scientific (Campro Scientific GmbH, Berlin, Germany)

Synthesis of Bromoacetic acid [$^{13}C_2$]-benzyl ester 3

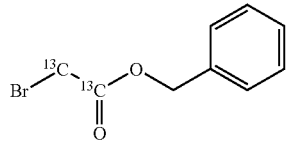 [SMILES: O=[13C]([13CH2]Br)OCc1ccccc1]

1.93 g (13.89 mMol) bromoacetic acid [$^{13}C_2$] (2), in 50 ml $CH_2Cl_2$ was mixed with 1.54 ml (14.88 mMol) benzylalcohol and 0.2 g (1.6 mMol) DMAP. After adding 3.07 g (14.88 mMol) dicyclohexylcarbodiimide to the solution at 0° C., the reaction mixture was stirred for 20 h at RT. The mixture was filtered and the residue was washed with $CH_2Cl_2$. 30 ml saturated $NaHCO_3$ solution was added to the filtrate. After shaking vigorously the solution for 5 minutes, the organic layer was isolated and the aqueous phase was extracted with $CH_2Cl_2$. The combined organic phase was dried over magnesium sulphate and the solvent was evaporated. The product (3) was subjected to a chromatographic purification using $CH_2Cl_2$.

Yield: 2.97 g (93.2%)
$R_F$=0.85 ($CH_2Cl_2$)

Dimethylamino-acetic acid [$^{13}C_4, ^{15}N$]-benzyl ester 4

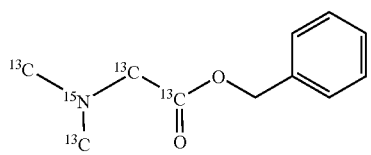

5.28 ml (13.2 mMol) 2.5 M BuLi in toluene was added dropwise at −50° C. to 1.05 g (12.88 nMol) dimethylamine [$^{13}C_2, ^{15}N$]-hydrochloride (1) dissolved in 40 ml THF. The reaction mixture was stirred until the reaction temperature reached −10° C. to obtain a solution. The solution was cooled down to −50° C. again and mixed with 2.26 ml (13.2 nMol) diisopropyl ethylamine. 2.97 g (13 mMol) Bromoacetic acid [$^{13}C_2$]-benzylester (3), in 15 ml THF was added dropwise to the mixture within 30 min. The reaction mixture was then left for 4h in the cooled bath and then stirred for 20 h at RT. After evaporation of the solvent under reduced pressure, the residue was dissolved in ca. 40 ml $NaHCO_3$-solution. The reaction mixture was extracted several times with EtOAc and the organic phase was dried over magnesium sulphate. After evaporation of the solvent, the residue was subjected to a chromatographic purification using EtOAc.

Yield: 1.27 g (50%)
$R_F$=0.3 (EtOAc)

Dimethylamino-acetic acid [$^{13}C_4, ^{15}N$] 5

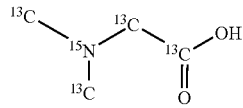

1.27 g (6.4 mMol) dimethylamino-acetic acid [$^{13}C_4, ^{15}N$]-benzyl ester 4 was stirred with 250 mg Pd/C (5%) in 100 ml methanol at RT. Under normal pressure, the reaction mixture was hydrated with $H_2$ for 30 min. After having removed the catalyst by filtration, the solution was evaporated to afford a white compound.

Yield: 0.62 g (94%)

Dimethylamino-acetic acid [$^{13}C_4, ^{15}N$]-(2,5-dioxo-pyrrolidin-1-yl)-ester 6

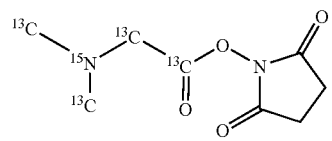

0.65 g (~6.4 mMol) dimethylamino-acetic acid 5 was added to 0.74 g (6.4 mMol) N-hydroxysuccinimide and 1.38 g (6.7 mMol) dicyclohexylcarbodiimide in 25 ml $CH_2Cl_2$. The reaction mixture was stirred for 20 at RT. The mixture was diluted with 70 ml diisopropylether, stirred for 1 h and filtered. The residue was then washed with 25 ml diisopropylether and the filtrate was evaporated in vacuum to dryness. The residue was then dissolved in ca. 10 ml $CH_2Cl_2$ und the solution was added under stirring to 230 ml diisopropylether at −5° C. After stirring for 1 h at −5° C., the solution was filtered, evaporated under reduced pressure. The residue was recrystallized from ca. 50 ml diisopropylether.

Yield: 0.71 g (54%)
Mp: 63° C.

7. Protocol for the Quantitative Analysis of a Test Protein with a Basic Mass Tag Cyanogen precleavage step: A protocol that is generally applicable to biological samples was used. 1 mg of a commercially available protein, Albumin Bovine (Sigma) was dissolved in 1 ml of a 90% formic acid solution. 1 mg cyanogen bromide (CNBr, 5 M in acetonitrile) was added to the solution. After shaking the reaction mixture for 20 h in the dark, the solution was diluted to 10 ml, frozen and lyophilised.

Reduction and alkylation step: The remaining residue was dissolved in 1100 µl of a denaturing buffer (100 mM borate puffer, 0.4 M urea, 0.2 M thiourea, and 0.4 M guanidine hydrochloride, pH 7.3), to which 25 µl of a 100 mM tris[2-carboxyethylphosphine] TCEP (Pierce) was added. After shaking for 30 min., 75 µl of a 200 mM iodoacetamide solution (Sigma) was added, and the reaction mixture was shaken for additional 2 h.

Protein labelling step: The solution was then divided equally in 2 portions of 600 µl each. One portion was incubated with 150 µl of DMG [$^{13}C_4,^{15}N$] label dissolved in DMF (2 M) for 3 h while the other portion was incubated with 150 µl of DMG [$^{12}C_4\ ^{14}N$] label dissolved in DMF (2 M) for the same time. After 3 h, a second portion of 150 µl of each DMG reagent dissolved in DMF (2 M), was added to their respective reaction mixture, and incubated overnight.

Protein pooling step: At that stage, after the labelling reaction, the 2 different labelled polypeptide mixtures were acidified with 1 µl TFA and portions of the two mixtures containing polypeptides labelled with DMG [$^{12}C_4\ ^{14}N$] label and DMG [$^{13}C_4\ ^{15}N$] label were mixed together to create predefined ratios.

Protein purification and digest step: To remove all of excess labelling reagents, the guanidine hydrochloride and the DMF, the mixtures of different labelled polypeptide ratios were purified by size exclusion centrifugation using Centricon devices with MWCO of 5000. A 50 mM portion of borate buffer pH 7.5 containing 66 mM urea and 33 mM thiourea was used for repeated dilution and recovery. 250 µl was recovered for each ratio. A 5 µg portion of trypsin (seq. grade modified trypsin, Promega) was added to each mixture, the pH was adjusted to 7.8 and the solution was incubated at 37° C. for 20 hours.

Prior to MS analysis, the labelled polypeptides samples were purified by an extraction cartridge (HLB Oasis, Waters Corp., Milford, Mass. USA).

8. MS and MS/MS Analysis

Analyses were performed by liquid chromatography mass spectrometry using a Waters Q-tof II connected to a Waters CapLC System (Column: LC Packings (Dionex), 150×0.075 mm, 3 µm, 100Å PepMap C18; Solvents: 100% Water to 100 % Acetonitrile both with 0.1% Formic Acid).

Peptide identification was performed by CID (collision of selected peptide ions) followed by automatic interpretation of the MS/MS spectra by SEQUEST (Yates, J. R., 3rd; Eng, J. K.; McCormack, A. L., Anal Chem. 67(18) pages 3202-3210, "Mining genomes: correlating tandem mass spectra of modified and unmodified peptides to sequences in nucleotide databases", 1995; MacCoss, M. J.; Wu, C. C.; Yates, J. R., 3$^{rd}$, Anal Chem. 74(21) pages 5593-5599, "Probability-based validation of protein identifications using a modified SEQUEST algorithm", 2002).

The quantitative analyses of the peptide pairs were performed manually in the MS mode after integration of their isotopic pattern, the DMG [$^{12}C_4\ ^{14}N$] and the DMG [$^{13}C_4\ ^{15}N$] labelled peptide, respectively. Thus the comparison of the peak areas coming from the DMG [$^{12}C_4\ ^{14}N$] labelled peptide and the DMG [$^{13}C_4\ ^{15}N$] labelled peptide produced the observed ratio.

References

Adamczyk, M., J. C. Gebler, et al. (1999). "A simple method to identify cysteine residues by isotopic labelling and ion trap mass spectrometry." *Rapid Commun Mass Spectrom* 13(18): 1813-7.

Bartlet-Jones, M., W. A. Jeffery, et al. (1994). "Peptide ladder sequencing by mass spectrometry using a novel, volatile degradation reagent." *Rapid Commun Mass Spectrom* 8(9): 737-42.

Bonetto, V., A. C. Bergman, et al. (1997). "C-terminal sequence determination of modified peptides by MALDI MS." *J Protein Chem* 16(5): 371-374.

Brancia, F. L., A. Butt, et al. (2001). "A combination of chemical derivatisation and improved bioinformatic tools optimises protein identification for proteomics." *Electronphoresis* 22(3): 552-9.

Brancia, F. L., S. G. Oliver, et al. (2000). "Improved matrix-assisted laser desorption/ionisation mass spectrometric analysis of tryptic hydrolysates of proteins following guanidination of lysine-containing peptides." *Rapid Commun Mass Spectrom* 14(21): 2070-3.

Cardenas, M. S., E. van der Heeft, et al. (1997). "On-line derivatisation of peptides for improved sequence analysis by micro-column liquid chromatography coupled with electrospray ionisation-tandem mass spectrometry." *Rapid Commun Mass Spectrom* 11(12): 1271-8.

Gaskell, S. (1997). "Electrospray: Principles and Practice." *Journal of Mass Spectrometry* 32: 677-688.

Goodlett, D. R., J. E. Bruce, et al. (2000). "Protein identification with a single accurate mass of a cysteine-containing peptide and constrained database searching." *Anal Chem* 72(6): 1112-8.

Griffiths, W. J., I. Lindh, et al. (1995). "Negative-ion Electrospray Mass Spectra of Peptides Derivatised with 4-Aminonaphthalenesulphonic acid." *Rapid Commun Mass Spectrom* 9: 667-676.

Gygi, S. P., B. Rist, et al. (1999). "Quantitative analysis of complex protein mixtures using isotope-coded affinity tags." *Nat Biotechnol* 17(10): 994-9.

Han, D. K., J. Eng, et al. (2001). "Quantitative profiling of differentiation-induced microsomal proteins using isotope-coded affinity tags and mass spectrometry." *Nat Biotechnol* 19(10): 946-51.

Karas, M., M. Gluckmann, et al. (2000). "Ionisation in matrix-assisted laser desorption/ionisation: singly charged molecular ions are the lucky survivors." *J Mass Spectrom* 35(1): 1-12.

Kaufmann, R., P. Chaurand, et al. (1996). "Post-source decay and delayed extraction in matrix-assisted laser desorption/ionisation-reflectron time-of-flight mass spectrometry. Are there trade-offs?" *Rapid Commun Mass Spectrom* 10(10): 1199-208.

Keough, T., M. P. Lacey, et al. (2001). "Atmospheric pressure matrix-assisted laser desorption/ionisation ion trap mass spectrometry of sulphonic acid derivatised tryptic peptides." *Rapid Commun Mass Spectrom* 15(23): 2227-2239.

Liu, H., D. Lin, et al. (2002). "Multidimensional separations for protein/peptide analysis in the post-genomic era." *Biotechniques* 32(4): 898, 900, 902 passim -898, 900, 902 passim.

Mann, M., P. Hojrup, et al. (1993). "Use of mass spectrometric molecular weight information to identify proteins in sequence databases." *Biol Mass Spectrom* 22(6): 338-45.

Mizhiritskii, M. and Y. Shpernat (2002). "Trends in peptide chemistry." *Chimica Oggi/Chemistry Today*.

Moini, M. (2002). "Capillary electrophoresis mass spectrometry and its application to the analysis of biological mixtures." *Anal Bioanal Chem* 373(6): 466-80.

Morand, K. L., T. M. Burt, et al. (2001). "Advances in high-throughput mass spectrometry." *Curr Opin Drug Discov Devel* 4(6): 729-35.

Pappin, D. J. C., P. Höjrup, et al. (1993). "Rapid identification of proteins by peptide-mass fingerprinting." *Curr Biol* 3: 372-332.

Polce, M. J., D. Ren, et al. (2000). "Dissociation of the peptide bond in protonated peptides." *J Mass Spectrom* 35(12): 1391-8.

Roth, K. D., Z. H. Huang, et al. (1998). "Charge derivatisation of peptides for analysis by mass spectrometry." *Mass Spectrom Rev* 17(4): 255-74.

Schlosser, A. and W. D. Lehmann (2000). "Five-membered ring formation in unimolecular reactions of peptides: a key structural element controlling low-energy collision-induced dissociation of peptides." *J Mass Spectrom* 35(12): 1382-90.

Sechi, S. (2002). "A method to identify and simultaneously determine the relative quantities of proteins isolated by gel electrophoresis." *Rapid Commun Mass Spectrom* 16(15): 1416-24.

Sechi, S. and B. T. Chait (1998). "Modification of cysteine residues by alkylation. A tool in peptide mapping and protein identification." *Anal Chem* 70(24): 5150-8.

Shen, Y., S. J. Berger, et al. (2000). "High-efficiency capillary isoelectric focusing of peptides." *Anal Chem* 72(9): 2154-9.

Sherman, N. E., N. A. Yates, et al. (1995). *A novel N-terminal derivative designed to simplify peptide fragmentation.* Proc 43rd ASMS Conf Mass Spectrom Allied Topics, Atlanta, Ga.

Smolka, M. B., H. Zhou, et al. (2001). "Optimisation of the isotope-coded affinity tag-labelling procedure for quantitative proteome analysis." *Anal Biochem* 297(1): 25-31.

Steen, H. and M. Mann (2002). "Analysis of bromotryptophan and hydroxyproline modifications by high-resolution, high-accuracy precursor ion scanning utilizing fragment ions with mass-deficient mass tags." *Anal Chem* 74(24): 6230-6.

Stults, J. T. (1992). *Amino-terminal quaternary ammonium derivatives of peptides alter fragmentation by electrospray ionisation/low energy collisionally activated dissociation.* Proc 40th ASMS Conf Mass Spectrom Allied Topics, Wash., D.C.

Stults, J. T., R. Halualani, et al. (1989). *Amino-terminal derivatisation of peptides yields improved CAD spectra.* Proc 37th ASMS Conf Mass Spectrom Allied Topics, Miami Beach, Fla.

Tang, W., A. K. Harrata, et al. (1997). "Two-dimensional analysis of recombinant *E. coli* proteins using capillary isoelectric focusing electrospray ionisation mass spectrometry." *Anal Chem* 69(16): 3177-82.

Tang, X. J., P. Thibault, et al. (1993). "Fragmentation reactions of multiply-protonated peptides and implications for sequencing by tandem mass spectrometry with low-energy collision-induced dissociation." *Anal Chem* 65(20): 2824-2834.

Washburn, M. P., R. Ulaszek, et al. (2002). "Analysis of quantitative proteomic data generated via multidimensional protein identification technology." *Anal Chem* 74(7): 1650-7.

Washburn, M. P., D. Wolters, et al. (2001). "Large-scale analysis of the yeast proteome by multidimensional protein identification technology." *Nat Biotechnol* 19(3): 242-247.

Washburn, M. P. and J. R. Yates (2000). "Analysis of the microbial proteome." *Curr Opin Microbiol* 3(3): 292-297.

Wolters, D. A., M. P. Washburn, et al. (2001). "An automated multidimensional protein identification technology for shotgun proteomics." *Anal Chem* 73(23): 5683-5690.

Wysocki, V. H., G. Tsaprailis, et al. (2000). "Mobile and localized protons: a framework for understanding peptide dissociation." *J Mass Spectrom* 35(12): 1399-1406.

Yates, J. R., 3rd, S. Speicher, et al. (1993). "Peptide mass maps: a highly informative approach to protein identification." *Anal Biochem* 214(2): 397-408.

---

The invention claimed is:

1. An array of mass tags comprising: at least two mass tag reagents, each mass tag reagent in the array being adapted to label a molecule to be characterized by mass spectrometry and having the following formula:

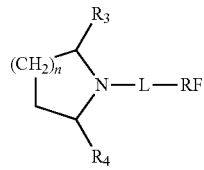

wherein $R^3$ and $R^4$ may be the same or different and are independently selected from alkyl groups;

the reactive functionality RF is selected from the group consisting of active esters of carbonic acids, alkenyl sulphones, haloalkanes, maleimides, isocyanates, isothiocyanates, ketones, aldehydes, sulphonyl-halides, carboxylic-halides, anhydride esters, alkenes, N-hydroxysuccinimide esters, hydroxybenzotriazole esters, hydroxyazabenzotriazole esters, nitrophenyl esters, trichlorophenyl esters and pentafluorophenyl esters; and the linker L is selected from —CH$_2$— and (CH$_2$)$_3$—, wherein each mass tag reagent in the array has a modified isotone distribution, wherein the isotope disiribution is modified via an isotope replacement selected from the group consisting of one or more of $^1$H by $^2$H, one or more of $^{12}$C by $^{13}$C, one or more of $^{16}$O by $^{18}$O and one or more of $^{14}$N by $^{15}$N.

2. An array of mass tags according to claim 1, wherein RF is selected from the group consisting of esters of carbonic acid, N-hydroxysuccinimide esters, hydroxybenzotriazole esters, hydroxyazabenzotriazole esters, nitrophenyl esters, trichlorophenyl esters and pentafluorophenyl esters.

3. An array of mass tags according to claim 1, wherein each mass tag reagent in the array has the same chemical structure and is an isotopomer of each other mass tag reagent in the array such that each mass tag reagent in the array has a different mass.

4. A kit for purification of labelled analyte molecules, which kit comprises one or more mass tag reagents as defined in claim 1, and a cation exchange resin.

5. A kit according to claim 4, which kit further comprises one or more components selected from a reaction buffer for the coupling of the mass tag reagent to analyte molecules, a buffer for washing the cation exchange resin, and a buffer for elution of the labelled peptides from the cation exchange resin.

6. An array of mass tag reagents according to claim 1, wherein each mass tag reagent in the array is adapted to label a protein.

7. An array of mass tags according to claim 1, wherein $R^3$ and $R^4$ are independently selected from methyl, ethyl, propyl and iso-propyl groups.

8. An array of mass tags according to claim 1, wherein n is 2.

* * * * *

SEQUENCE LISTING

<160> NUMBER OF SEQ ID NOS: 4

<210> SEQ ID NO 1
<211> LENGTH: 607
<212> TYPE: PRT
<213> ORGANISM: Bos taurus

<400> SEQUENCE: 1

```
Met Lys Trp Val Thr Phe Ile Ser Leu Leu Leu Leu Phe Ser Ser Ala
  1               5                  10                  15

Tyr Ser Arg Gly Val Phe Arg Arg Asp Thr His Lys Ser Glu Ile Ala
             20                  25                  30

His Arg Phe Lys Asp Leu Gly Glu Glu His Phe Lys Gly Leu Val Leu
         35                  40                  45

Ile Ala Phe Ser Gln Tyr Leu Gln Gln Cys Pro Phe Asp Glu His Val
     50                  55                  60

Lys Leu Val Asn Glu Leu Thr Glu Phe Ala Lys Thr Cys Val Ala Asp
 65                  70                  75                  80

Glu Ser His Ala Gly Cys Glu Lys Ser Leu His Thr Leu Phe Gly Asp
                 85                  90                  95
```

-continued

```
Glu Leu Cys Lys Val Ala Ser Leu Arg Glu Thr Tyr Gly Asp Met Ala
             100                 105                 110

Asp Cys Cys Glu Lys Gln Glu Pro Glu Arg Asn Glu Cys Phe Leu Ser
             115                 120                 125

His Lys Asp Asp Ser Pro Asp Leu Pro Lys Leu Lys Pro Asp Pro Asn
         130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                 165                 170                 175

Leu Leu Tyr Tyr Ala Asn Lys Tyr Asn Gly Val Phe Gln Glu Cys Cys
             180                 185                 190

Gln Ala Glu Asp Lys Gly Ala Cys Leu Leu Pro Lys Ile Glu Thr Met
             195                 200                 205

Arg Glu Lys Val Leu Ala Ser Ser Ala Arg Gln Arg Leu Arg Cys Ala
         210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                 245                 250                 255

Leu Val Thr Asp Leu Thr Lys Val His Lys Glu Cys Cys His Gly Asp
             260                 265                 270

Leu Leu Glu Cys Ala Asp Asp Arg Ala Asp Leu Ala Lys Tyr Ile Cys
             275                 280                 285

Asp Asn Gln Asp Thr Ile Ser Ser Lys Leu Lys Glu Cys Cys Asp Lys
         290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                 325                 330                 335

Asp Val Cys Lys Asn Tyr Gln Glu Ala Lys Asp Ala Phe Leu Gly Ser
             340                 345                 350

Phe Leu Tyr Glu Tyr Ser Arg Arg His Pro Glu Tyr Ala Val Ser Val
             355                 360                 365

Leu Leu Arg Leu Ala Lys Glu Tyr Glu Ala Thr Leu Glu Glu Cys Cys
         370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                 405                 410                 415

Gln Phe Glu Lys Leu Gly Glu Tyr Gly Phe Gln Asn Ala Leu Ile Val
             420                 425                 430

Arg Tyr Thr Arg Lys Val Pro Gln Val Ser Thr Pro Thr Leu Val Glu
         435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                 485                 490                 495

Thr Lys Cys Cys Thr Glu Ser Leu Val Asn Arg Arg Pro Cys Phe Ser
             500                 505                 510

Ala Leu Thr Pro Asp Glu Thr Tyr Val Pro Lys Ala Phe Asp Glu Lys
             515                 520                 525
```

```
Leu Phe Thr Phe His Ala Asp Ile Cys Thr Leu Pro Asp Thr Glu Lys
        530                 535                 540

Gln Ile Lys Lys Gln Thr Ala Leu Val Glu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
                580                 585                 590

Val Glu Gly Pro Lys Leu Val Val Ser Thr Gln Thr Ala Leu Ala
                595                 600                 605

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: dimethylglycine

<400> SEQUENCE: 2

Lys Xaa Val Pro Gln Val Ser Thr Pro Thr Leu Val Glu Val Ser Arg
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: dimethylglycine

<400> SEQUENCE: 3

Xaa Pro Cys Thr Glu Asp Tyr Leu Ser Leu Ile Leu Asn Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: dimethylglycine
<220> FEATURE:
<221> NAME/KEY: MOD_RES
<222> LOCATION: (6)
<223> OTHER INFORMATION: dimethylglycine

<400> SEQUENCE: 4

Xaa Ala Ala Leu Lys Xaa Ala Trp Ser Val Ala Arg
1               5                   10
```